US010725025B2

(12) United States Patent
Jatzke et al.

(10) Patent No.: US 10,725,025 B2
(45) Date of Patent: Jul. 28, 2020

(54) METHODS FOR ENHANCING THE SPECIFIC UPTAKE OF BOTULINUM NEUROTOXINS INTO CELLS

(71) Applicant: MERZ PHARMA GMBH & CO. KGAA, Frankfurt am Main (DE)

(72) Inventors: Claudia Jatzke, Frankfurt (DE); Karl-Heinz Eisele, Frankfurt am Main (DE); Gerd Mander, Frankfurt (DE); Klaus Fink, Cologne (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 0 days.

(21) Appl. No.: 15/554,338

(22) PCT Filed: Mar. 3, 2016

(86) PCT No.: PCT/EP2016/054552
§ 371 (c)(1),
(2) Date: Aug. 29, 2017

(87) PCT Pub. No.: WO2016/139308
PCT Pub. Date: Sep. 9, 2016

(65) Prior Publication Data
US 2018/0238861 A1    Aug. 23, 2018

(30) Foreign Application Priority Data

Mar. 4, 2015  (EP) .................................. 15157549

(51) Int. Cl.
| G01N 33/50 | (2006.01) |
| G01N 1/30 | (2006.01) |
| C09J 7/40 | (2018.01) |
| A47L 9/00 | (2006.01) |
| G02B 5/30 | (2006.01) |
| G02F 1/1335 | (2006.01) |
| B32B 43/00 | (2006.01) |
| B32B 38/10 | (2006.01) |

(52) U.S. Cl.
CPC ............ *G01N 33/5058* (2013.01); *A47L 9/00* (2013.01); *C09J 7/40* (2018.01); *G01N 1/30* (2013.01);
(Continued)

(58) Field of Classification Search
None
See application file for complete search history.

(56) References Cited

U.S. PATENT DOCUMENTS

2008/0032931 A1* 2/2008 Steward .................. C07K 1/22
514/1.2
2010/0216181 A1    8/2010  Daigh et al.
(Continued)

FOREIGN PATENT DOCUMENTS

| CA | 2978225 A1 * | 9/2016 | ............... A47L 9/00 |
| EP | 1700918 A2 * | 9/2006 | ............. C07K 14/33 |

(Continued)

OTHER PUBLICATIONS

Altschul et al., "Basic Local Alignment Search Tool", J. Mol. Biol. (1990) 215, 403-410.
(Continued)

*Primary Examiner* — Nita M. Minnifield
(74) *Attorney, Agent, or Firm* — J.A. Lindeman & Co., PLLC

(57) ABSTRACT

The present invention provides a method for enhancing the specific uptake of a neurotoxin polypeptide into cells, the method comprising: incubating cells susceptible to neurotoxin intoxication with a neurotoxin polypeptide for a time and under conditions which allow for the neurotoxin polypeptide to exert its biological activity, the incubation comprising at least one of the following steps: (i) $K^+$-mediated depolarization of the cells, (ii) a reduced neurotoxin polypeptide exposition time and/or (iii) agitation of the cells during neurotoxin polypeptide exposition, thereby enhancing the specific uptake of the neurotoxin polypeptide into said cells. In addition, the invention pertains to a method for directly determining the biological activity of a neurotoxin polypeptide in cells, comprising: a) incubating cells susceptible to neurotoxin intoxication with a neurotoxin polypeptide for a time and under conditions which allow for the neurotoxin polypeptide to exert its biological activity, the incubation comprising at least one of the following steps: (i) $K^+$-mediated depolarization of the cells, (ii) a reduced neurotoxin polypeptide exposition time and/or (iii) agitation of the cells during neurotoxin polypeptide exposition; b) fixing the cells and, optionally, permeabilizing the cells with a detergent; c) contacting the cells with at least a first capture antibody specifically binding to the non-cleaved and neurotoxin-cleaved substrate and with at least a second capture antibody specifically binding to the cleavage site of the neurotoxin-cleaved substrate, under conditions which allow for binding of said capture antibodies to said substrates; d) contacting the cells with at least a first detection antibody specifically binding to the first capture antibody, under conditions which allow for binding of said first detection antibody to said first capture antibody, thus forming first detection complexes and with at least a second detection antibody specifically binding to the second capture antibody, under conditions which allow for binding of said second detection antibody to said second capture antibody, thus forming second detection complexes; e) determining the amount of the first and second detection complexes of step d); and f) calculating the amount of substrate cleaved by said neurotoxin polypeptide in said cells by means of the second detection complexes, thereby determining the biological activity of said neurotoxin polypeptide in said cells.

25 Claims, 1 Drawing Sheet

Specification includes a Sequence Listing.

(52) U.S. Cl.
CPC ............. *G02B 5/30* (2013.01); *G02F 1/1335* (2013.01); *B32B 38/10* (2013.01); *B32B 43/006* (2013.01); *G01N 2333/33* (2013.01); *Y10T 156/1132* (2015.01); *Y10T 156/1174* (2015.01); *Y10T 156/1195* (2015.01); *Y10T 156/195* (2015.01); *Y10T 156/1944* (2015.01); *Y10T 156/1994* (2015.01)

(56) References Cited

U.S. PATENT DOCUMENTS

| | | |
|---|---|---|
| 2010/0279403 A1 | 11/2010 | Rajesh et al. |
| 2012/0122128 A1 | 5/2012 | Fernandez-Salas et al. |
| 2012/0282647 A1* | 11/2012 | Mander .............. G01N 33/5088 435/29 |
| 2016/0289731 A1* | 10/2016 | Eisele ................ C07K 14/4702 |
| 2018/0045733 A1* | 2/2018 | Eisele .............. G01N 33/56911 |
| 2018/0238861 A1* | 8/2018 | Jatzke ........................ A47L 9/00 |
| 2019/0023771 A1* | 1/2019 | Bruenn .................. C07K 16/18 |

FOREIGN PATENT DOCUMENTS

| | | |
|---|---|---|
| JP | 2011500075 A | 1/2011 |
| WO | 2009/053536 A2 | 4/2009 |
| WO | 2009/114748 A1 | 9/2009 |
| WO | 2010/105234 A1 | 9/2010 |
| WO | 2011/025852 A1 | 3/2011 |
| WO | 2011/056971 A2 | 5/2011 |
| WO | 2012/135621 A2 | 10/2012 |
| WO | 2014/079878 A1 | 5/2014 |
| WO | 2014/207109 A1 | 12/2014 |
| WO | WO-2016139308 A1 * | 9/2016 ............... A47L 9/00 |

OTHER PUBLICATIONS

David. A. Armbruster and Terry Pry "Limit of Blank, Limit of Detection and Limit of Quantitation", Clin. Biochem. Rev. vol. 29, Suppl. (i) 2008, S49-S52.

Arnon et al., "Botulinum Toxin as a Biological Weapon", JAMA, 2001, vol. 285, No. 8, 1059-1070.

Jason S. Barash and Stephen S. Arnon "A Novel Strain of Clostridium botulinum That Produces Type B and Type H Botulinum Toxins", J. Infect. Dis. 2014, 209(2), 183-191.

Couesnon et al., "Expression of botulinum neurotoxins A and E. and associated non-toxin genes, during the transition phase and stability at high temperature: analysis by quantitative reverse transcription—PCR", Microbiology, 2006, 152, 759-770.

Dover et al., "Molecular Characterization of a Novel Botulinum Neurotoxin Type H Gene", J. Infect. Dis., 2014, 209 (2), 192-202.

Dressler et al., "Mouse Diaphragm Assay for Detection of Antibodies Against Botulinum Toxin Type B", Movement Dis. 2005, vol. 20, No. 12, 1617-1619.

Fernandez-Salas et al., "Botulinum Neurotoxin Serotype a Specific Cell-Based Potency Assay to Replace the Mouse Bioassay", PLOS One, 2012, vol. 7, Issue 11, e49516.

Audrey Discher and Mauricio Montal "Single molecule detection of intermediates during botulinum neurotoxin translocation across membranes", PNAS, 2007, vol. 104, No. 25, 10447-10452.

Higgins 1989, Cabios 5, 151.

Hill et al., "Genetic Diversity among Botulinum Neurotoxin-Producing Clostridial Strains", J. Bacteriol., 2007, vol. 189, No. 3, 818-832.

International Preliminary Report on Patentability in International Application No. PCT/EP2016/054452, dated Sep. 14, 2017.

Jacky et al., "Identification of Fibroblast Growth Factor Receptor 3 (FGFR3) as a Protein Receptor for Botulinum Neurotoxin Serotype A (BoNT/A)", PLOS One, 2013, vol. 9, Issue 5, e1003369.

Jost et al., "Botulinum Neurotoxin Type A Free of Complexing Proteins (XEOMIN) in Focal Dystonia", Drugs, 2007, 67 (5): 669-683.

J.E. Keller "Recovery From Botulinum Neurotoxin Poisoning in Vivo", Neuroscience, 139, (2006), 629-637.

Krieglstein et al., "Arrangement of disulfide bridges and positions of sulfhydryl groups in tetanus toxin", Eur. J. Biochem., (1990), 188, 39-45.

Krieglstein et al., "Limited proteolysis of tetanus toxin", Eur. J. Biochem., (1991), 202, 41-51.

Krieglstein et al., "Covalent Structure of Botulinum Neurotoxin Type A: Location of Sulfhydryl Groups, and Disulfide Bridges and Identification of C-Termini of Light and Heavy Chains", J. Protein Chem., (1994), vol. 13, No. 1, 49-57.

Kroken et al., "Novel Ganglioside-mediated Entry of Botulinum Neurotoxin Serotype D into Neurons", J. Biolog. Chem., (2011), vol. 286, No. 30, 26828-26837.

Saul B. Needleman and Christian D. Wunsch "A General Method Applicable to the Search for Similarities in the Amino Acid Sequence of Two Proteins", J. Mol. Bio., (1970), 48, 443-453.

Pearce et al., "Measurement of Botulinum Toxin Activity: Evaluation of the Lethality Assay", Toxicol. Appl. Pharmacol., (1994), 128, 69-77.

Pellett et al., "Sensitive and quantitative detection of botulinum neurotoxin in neurons derived from mouse embryonic stem cells", Biochem. Biophys. Res. Commun. 2011, 404(1): 388-392.

T.K. Sawyer "Peptidomimetic Design and Chemical Approaches to Peptide Metabolism: Peptide Based Drug Design: Controlling Transport and Metabolism", Taylor and Amidon, Eds. Washington, DC, ACS, Chapter 17, pp. 387-422 (1995).

Stephen Silberstein "Botulinum Neurotoxins: Origins and Basic Mechanisms of Action", Pain Practice, 2004, vol. 4, Issue 1S, S19-S26.

Temple F. Smith "Comparison of Biosequences", Adv. Appl. Math. 2 (1981), 482-489.

Donald W. Straughan "Progress in Applying the Three Rs to the Potency Testing of Botulinum Toxin Type A", ATLA 34, (2006), 305-313.

Whitemarsh et al., "Novel Application of Human Neurons Derived from Induced Pluripotent Stem Cells for Highly Sensitive Botulinum Neurotoxin Detection", Toxicol. Sci., (2012), 126(2), 426-435.

Yu et al., "Human Induced Pluripotent Stem Cells Free of Vector and Transgene Sequences", Science, 2009, 324 (5928): 797-801.

Keller et al., "Uptake of Botunlinum Neurotoxin into Cultured Neurons", Biochemistry, 2004, 43, pp. 526-532.

Sabina Pellett "Progress in Cell Based Assays for Botulinum Neurotoxin Detection", Curr Top Microbiol Immunol. 2013, 364: 257-285.

Vlaev et al., "Submerged culture process for biomass and exopolysaccharide production by Antarctic yeast: some engineering considerations", Appl Microbiol. Biotechnol., 2013, 97: 5303-5313.

* cited by examiner

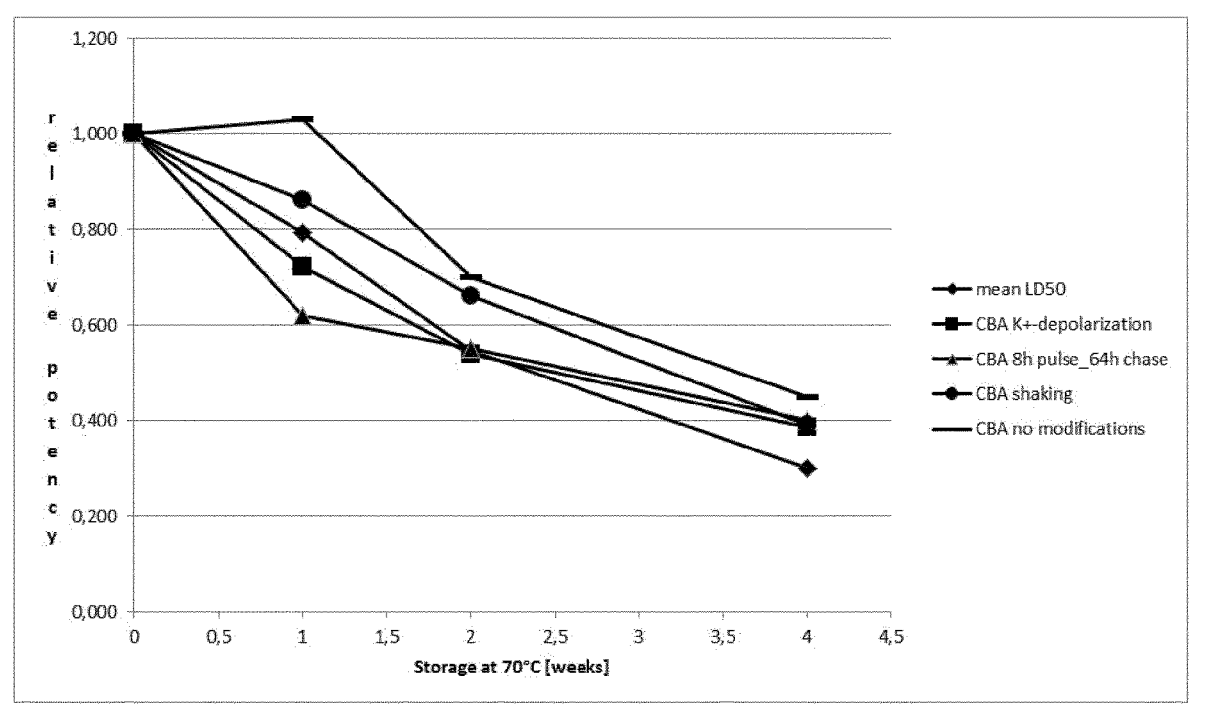

SEQUENCE LISTING

```
<160> NUMBER OF SEQ ID NOS: 16

<210> SEQ ID NO 1
<211> LENGTH: 3891
<212> TYPE: DNA
<213> ORGANISM: Clostridium botulinum

<400> SEQUENCE: 1
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agattttaat     180
ccaccaccag aagcaaaaca agttccagtt tcatattatg attcaacata tttaagtaca     240
```

```
gataatgaaa aagataatta tttaaaggga gttacaaaat tatttgagag aatttattca    300
actgatcttg gaagaatgtt gttaacatca atagtaaggg gaataccatt ttggggtgga    360
agtacaatag atacagaatt aaaagttatt gatactaatt gtattaatgt gatacaacca    420
gatggtagtt atagatcaga agaacttaat ctagtaataa taggaccctc agctgatatt    480
atacagtttg aatgtaaaag ctttggacat gaagttttga atcttacgcg aaatggttat    540
ggctctactc aatacattag atttagccca gattttacat ttggttttga ggagtcactt    600
gaagttgata caaatcctct tttaggtgca ggcaaatttg ctacagatcc agcagtaaca    660
ttagcacatg aacttataca tgctggacat agattatatg gaatagcaat taatccaaat    720
agggttttta aagtaaatac taatgcctat tatgaaatga gtgggttaga agtaagcttt    780
gaggaactta gaacatttgg gggacatgat gcaaagttta tagatagttt acaggaaaac    840
gaatttcgtc tatattatta taataagttt aaagatatag caagtacact taataaagct    900
aaatcaatag taggtactac tgcttcatta cagtatatga aaaatgtttt taaagagaaa    960
tatctcctat ctgaagatac atctggaaaa ttttcggtag ataaattaaa atttgataag    1020
ttatacaaaa tgttaacaga gatttacaca gaggataatt ttgttaagtt ttttaaagta    1080
cttaacagaa aaacatattt gaattttgat aaagccgtat ttaagataaa tatagtacct    1140
aaggtaaatt acacaatata tgatggattt aatttaagaa atacaaattt agcagcaaac    1200
tttaatggtc aaaatacaga aattaataat atgaatttta ctaaactaaa aaattttact    1260
ggattgtttg aattttataa gttgctatgt gtaagaggga taataacttc taaaactaaa    1320
tcattagata aaggatacaa taaggcatta aatgatttat gtatcaaagt taataattgg    1380
gacttgtttt ttagtccttc agaagataat tttactaatg atctaaataa aggagaagaa    1440
attacatctg atactaatat agaagcagca gaagaaaata ttagtttaga tttaatacaa    1500
caatattatt taacctttaa ttttgataat gaacctgaaa atatttcaat agaaaatctt    1560
tcaagtgaca ttataggcca attagaactt atgcctaata tagaaagatt tcctaatgga    1620
aaaaagtatg agttagataa atatactatg ttccattatc ttcgtgctca agaatttgaa    1680
catggtaaat ctaggattgc tttaacaaat tctgttaacg aagcattatt aaatcctagt    1740
cgtgtttata catttttttc ttcagactat gtaaagaaag ttaataaagc tacggaggca    1800
gctatgtttt taggctgggt agaacaatta gtatatgatt ttaccgatga aactagcgaa    1860
gtaagtacta cggataaaat tgcggatata actataatta ttccatatat aggacctgct    1920
ttaaatatag gtaatatgtt atataaagat gattttgtag gtgctttaat attttcagga    1980
gctgttattc tgttagaatt tataccagag attgcaatac ctgtattagg tacttttgca    2040
cttgtatcat atattgcgaa taaggttcta accgttcaaa caatagataa tgctttaagt    2100
aaaagaaatg aaaaatggga tgaggtctat aaatatatag taacaaattg gttagcaaag    2160
gttaatacac agattgatct aataagaaaa aaaatgaaag aagctttaga aaatcaagca    2220
gaagcaacaa aggctataat aaaactatcag tataatcaat atactgagga agagaaaaat    2280
aatattaatt ttaatattga tgatttaagt tcgaaactta atgagtctat aaataaagct    2340
atgattaata taaataaatt tttgaatcaa tgctctgttt catatttaat gaattctatg    2400
atcccttatg gtgttaaacg gttagaagat tttgatgcta gtcttaaaga tgcattatta    2460
aagtatatat atgataatag aggaaccttta attggtcaag tagatagatt aaaagataaa    2520
gttaataata cacttagtac agatataccct tttcagcttt ccaaatacgt agataatcaa    2580
```

-continued

```
agattattat ctacatttac tgaatatatt aagaatatta ttaatacttc tatattgaat    2640
ttaagatatg aaagtaatca tttaatagac ttatctaggt atgcatcaaa aataaatatt    2700
ggtagtaaag taaattttga tccaatagat aaaaatcaaa ttcaattatt taatttagaa    2760
agtagtaaaa ttgaggtaat tttaaaaaat gctattgtat ataatagtat gtatgaaaat    2820
tttagtacta gcttttggat aagaattcct aagtatttta acagtataag tctaaataat    2880
gaatatacaa taataaattg tatggaaaat aattcaggat ggaaagtatc acttaattat    2940
ggtgaaataa tctggacttt acaggatact caggaaataa aacaaagagt agttttaaa     3000
tacagtcaaa tgattaatat atcagattat ataaacagat ggattttgt aactatcact     3060
aataatagat taaataactc taaaatttat ataaatggaa gattaataga tcaaaaacca    3120
atttcaaatt taggtaatat tcatgctagt aataatataa tgtttaaatt agatggttgt    3180
agagatacac atagatatat ttggataaaa tattttaatc tttttgataa ggaattaaat    3240
gaaaagaaa tcaaagattt atatgataat caatcaaatt caggtatttt aaaagacttt     3300
tgggtgatt atttacaata tgataaacca tactatatgt taaatttata tgatccaaat     3360
aaatatgtcg atgtaaataa tgtaggtatt agaggttata tgtatcttaa agggcctaga    3420
ggtagcgtaa tgactacaaa catttattta aattcaagtt tgtataggg gacaaaattt     3480
attataaaaa aatatgcttc tggaaataaa gataatattg ttagaaataa tgatcgtgta    3540
tatattaatg tagtagttaa aaataaagaa tataggttag ctactaatgc atcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa tatagctaaa    3780
ctagtagcaa gtaattggta taatagacaa atagaaagat ctagtaggac tttgggttgc    3840
tcatgggaat ttattcctgt agatgatgga tggggagaaa ggccactgta a            3891
```

<210> SEQ ID NO 2  
<211> LENGTH: 1296  
<212> TYPE: PRT  
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140
```

```
Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
            165                 170                 175

Arg Asn Gly Tyr Gly Ser Thr Gln Tyr Ile Arg Phe Ser Pro Asp Phe
        180                 185                 190

Thr Phe Gly Phe Glu Glu Ser Leu Glu Val Asp Thr Asn Pro Leu Leu
    195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
        260                 265                 270

Phe Ile Asp Ser Leu Gln Glu Asn Glu Phe Arg Leu Tyr Tyr Tyr Asn
    275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
        340                 345                 350

Asn Phe Val Lys Phe Phe Lys Val Leu Asn Arg Lys Thr Tyr Leu Asn
    355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
        420                 425                 430

Gly Ile Ile Thr Ser Lys Thr Lys Ser Leu Asp Lys Gly Tyr Asn Lys
    435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
        500                 505                 510

Glu Asn Ile Ser Ile Glu Asn Leu Ser Ser Asp Ile Ile Gly Gln Leu
    515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
```

-continued

```
                565                 570                 575
Leu Asn Pro Ser Arg Val Tyr Thr Phe Phe Ser Ser Asp Tyr Val Lys
                580                 585                 590
Lys Val Asn Lys Ala Thr Glu Ala Ala Met Phe Leu Gly Trp Val Glu
                595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
                660                 665                 670
Ile Pro Val Leu Gly Thr Phe Ala Leu Val Ser Tyr Ile Ala Asn Lys
                675                 680                 685
Val Leu Thr Val Gln Thr Ile Asp Asn Ala Leu Ser Lys Arg Asn Glu
                690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
                740                 745                 750
Gln Tyr Thr Glu Glu Lys Asn Asn Ile Asn Phe Asn Ile Asp Asp
                755                 760                 765
Leu Ser Ser Lys Leu Asn Glu Ser Ile Asn Lys Ala Met Ile Asn Ile
    770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
                820                 825                 830
Gln Val Asp Arg Leu Lys Asp Lys Val Asn Asn Thr Leu Ser Thr Asp
                835                 840                 845
Ile Pro Phe Gln Leu Ser Lys Tyr Val Asp Asn Gln Arg Leu Leu Ser
    850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
                900                 905                 910
Gln Ile Gln Leu Phe Asn Leu Glu Ser Ser Lys Ile Glu Val Ile Leu
                915                 920                 925
Lys Asn Ala Ile Val Tyr Asn Ser Met Tyr Glu Asn Phe Ser Thr Ser
                930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                965                 970                 975
Ser Leu Asn Tyr Gly Glu Ile Ile Trp Thr Leu Gln Asp Thr Gln Glu
                980                 985                 990
```

Ile Lys Gln Arg Val Val Phe Lys Tyr Ser Gln Met Ile Asn Ile Ser
    995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 3
<211> LENGTH: 3876
<212> TYPE: DNA
<213> ORGANISM: Clostridium botulinum

<400> SEQUENCE: 3
atgccagtta caataaataa ttttaattat aatgatccta ttgataataa taatattatt    60
atgatggagc ctccatttgc gagaggtacg gggagatatt ataaagcttt taaaatcaca   120
gatcgtattt ggataatacc ggaaagatat acttttggat ataaacctga ggattttaat   180
aaaagttccg gtattttaa tagagatgtt tgtgaatatt atgatccaga ttacttaaat   240

```
actaatgata aaaagaatat attttacaa acaatgatca agttatttaa tagaatcaaa      300
tcaaaaccat tgggtgaaaa gttattagag atgattataa atggtatacc ttatcttgga      360
gatagacgtg ttccactcga agagtttaac acaaacattg ctagtgtaac tgttaataaa      420
ttaatcagta atccaggaga agtggagcga aaaaaaggta ttttcgcaaa tttaataata      480
tttggacctg ggccagtttt aaatgaaaat gagactatag ataggtat acaaaatcat       540 tttgcatcaa gggaaggctt cggggtata atgcaaatga agttttgccc agaatatgta      600
agcgtattta ataatgttca agaaaacaaa ggcgcaagta tatttaatag acgtggatat      660
ttttcagatc cagccttgat attaatgcat gaacttatac atgttttaca tggattatat      720
ggcattaaag tagatgattt accaattgta ccaaatgaaa aaaaattttt tatgcaatct      780
acagatgcta tacaggcaga agaactatat acatttggag acaagatcc cagcatcata      840 actccttcta cggataaaag tatctatgat aaagttttgc aaaattttag agggatagtt      900
gatagactta acaaggtttt agtttgcata tcagatccta acattaatat taatatatat       960
aaaaataaat ttaaagataa atataaattc gttgaagatt ctgagggaaa atatagtata     1020
gatgtagaaa gttttgataa attatataaa agcttaatgt ttggttttac agaaactaat     1080
atagcagaaa attataaaat aaaaactaga gcttcttatt ttagtgattc cttaccacca     1140
gtaaaaataa aaattttatt agataatgaa atctatacta tagaggaagg gtttaatata     1200
tctgataaag atatggaaaa agaatataga ggtcagaata aagctataaa taaacaagct     1260
tatgaagaaa ttagcaagga gcatttggct gtatataaga tacaaatgtg taaaagtgtt     1320
aaagctccag gaatatgtat tgatgttgat aatgaagatt tgttctttat agctgataaa     1380
aatagttttt cagatgattt atctaaaaac gaaagaatag aatataatac acagagtaat     1440
tatatagaaa atgacttccc tataaatgaa ttaattttag atactgattt aataagtaaa     1500
atagaattac caagtgaaaa tacagaatca cttactgatt ttaatgtaga tgttccagta     1560
tatgaaaaac aacccgctat aaaaaaaatt tttacagatg aaaataccat cttttcaatat     1620 ttatactctc agacatttcc tctagatata agagatataa gtttaacatc ttcatttgat     1680
gatgcattat tattttctaa caaagtttat tcatttttt ctatggatta tattaaaact      1740
gctaataaag tggtagaagc aggattattt gcaggttggg tgaaacagat agtaaatgat     1800
tttgtaatcg aagctaataa aagcaatact atggataaaa ttgcagatat atctctaatt     1860
gttccttata taggattagc tttaaatgta ggaaatgaaa cagctaaagg aaattttgaa     1920
aatgcttttg agattgcagg agccagtatt ctactagaat ttataccaga acttttaata     1980
cctgtagttg gagcctttt attagaatca tatattgaca ataaaaataa aattattaaa     2040
acaatagata atgctttaac taaaagaaat gaaaaatgga gtgatatgta cggattaata     2100
gtagcgcaat ggctctcaac agttaatact caattttata caataaaaga gggaatgtat     2160
aaggctttaa attatcaagc acaagcattg gaagaaataa taaaatacag atataatata     2220
tattctgaaa aagaaaagtc aaatattaac atcgatttta atgatataaa ttctaaactt     2280
aatgagggta ttaaccaagc tatagataat ataaataatt ttataaatgg atgttctgta     2340
tcatatttaa tgaaaaaaat gattccatta gctgtagaaa aattactaga cttgataat       2400 actctcaaaa aaatttgtt aaattatata gatgaaaata aattatattt gattggaagt      2460
gcagaatatg aaaaatcaaa agtaaataaa tacttgaaaa ccattatgcc gtttgatctt     2520
tcaatatata ccaatgatac aatactaata gaaatgttta taaatataa tagcgaaatt       2580
```

```
ttaaataata ttatcttaaa tttaagatat aaggataata atttaataga tttatcagga    2640
tatggggcaa aggtagaggt atatgatgga gtcgagctta atgataaaaa tcaatttaaa    2700
ttaactagtt cagcaaatag taagattaga gtgactcaaa atcagaatat catatttaat    2760
agtgtgttcc ttgattttag cgttagcttt tggataagaa tacctaaata taagaatgat    2820
ggtatacaaa attatattca taatgaatat acaataatta attgtatgaa aaataattcg    2880
ggctggaaaa tatctattag gggtaatagg ataatatgga ctttaattga tataaatgga    2940
aaaaccaaat cggtattttt tgaatataac ataagagaag atatatcaga gtatataaat    3000
agatggtttt ttgtaactat tactaataat ttgaataacg ctaaaattta tattaatggt    3060
aagctagaat caaatacaga tattaaagat ataagagaag ttattgctaa tggtgaaata    3120
atatttaaat tagatggtga tatagataga acacaattta tttggatgaa atatttcagt    3180
atttttaata cggaattaag tcaatcaaat attgaagaaa gatataaaat tcaatcatat    3240
agcgaatatt taaagatttt tggggaaat cctttaatgt acaataaaga atattatatg    3300
tttaatgcgg ggaataaaaa ttcatatatt aaactaaaga aagattcacc tgtaggtgaa    3360
attttaacac gtagcaaata taatcaaaat tctaaatata taaattatag agatttatat    3420
attggagaaa aatttattat aagaagaaag tcaaattctc aatctataaa tgatgatata    3480
gttagaaaag aagattatat atatctagat tttttttaatt taaatcaaga gtggagagta    3540
tatacctata aatattttaa gaagaggaa gaaaaattgt ttttagctcc tataagtgat    3600
tctgatgagt tttacaatac tatacaaata aaagaatatg atgaacagcc aacatatagt    3660
tgtcagttgc tttttaaaaa agatgaagaa agtactgatg agataggatt gattggtatt    3720
catcgtttct acgaatctgg aattgtattt gaagagtata agattatttt ttgtataagt    3780
aaatggtact aaaagaggt aaaaaggaaa ccatataatt taaaattggg atgtaattgg    3840
cagtttattc ctaaagatga agggtggact gaataa                              3876
```

<210> SEQ ID NO 4
<211> LENGTH: 1291
<212> TYPE: PRT
<213> ORGANISM: Clostridium botulinum

<400> SEQUENCE: 4

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

```
Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
            165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
            245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
            405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
            485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
```

-continued

```
                565                 570                 575
Tyr Ile Lys Thr Ala Asn Lys Val Val Glu Ala Gly Leu Phe Ala Gly
                580                 585                 590

Trp Val Lys Gln Ile Val Asn Asp Phe Val Ile Glu Ala Asn Lys Ser
                595                 600                 605

Asn Thr Met Asp Lys Ile Ala Asp Ile Ser Leu Ile Val Pro Tyr Ile
                610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
                675                 680                 685

Arg Asn Glu Lys Trp Ser Asp Met Tyr Gly Leu Ile Val Ala Gln Trp
                690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
                755                 760                 765

Asp Asn Ile Asn Asn Phe Ile Asn Gly Cys Ser Val Ser Tyr Leu Met
                770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
                835                 840                 845

Leu Ile Glu Met Phe Asn Lys Tyr Asn Ser Glu Ile Leu Asn Asn Ile
                850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asn Ile Ile Phe Asn Ser Val Phe Leu Asp Phe Ser Val
                915                 920                 925

Ser Phe Trp Ile Arg Ile Pro Lys Tyr Lys Asn Asp Gly Ile Gln Asn
                930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
                980                 985                 990
```

```
Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu
    1010                1015                1020

Ser Asn Thr Asp Ile Lys Asp Ile Arg Glu Val Ile Ala Asn Gly
    1025                1030                1035

Glu Ile Ile Phe Lys Leu Asp Gly Asp Ile Asp Arg Thr Gln Phe
    1040                1045                1050

Ile Trp Met Lys Tyr Phe Ser Ile Phe Asn Thr Glu Leu Ser Gln
    1055                1060                1065

Ser Asn Ile Glu Glu Arg Tyr Lys Ile Gln Ser Tyr Ser Glu Tyr
    1070                1075                1080

Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
    1100                1105                1110

Lys Asp Ser Pro Val Gly Glu Ile Leu Thr Arg Ser Lys Tyr Asn
    1115                1120                1125

Gln Asn Ser Lys Tyr Ile Asn Tyr Arg Asp Leu Tyr Ile Gly Glu
    1130                1135                1140

Lys Phe Ile Ile Arg Arg Lys Ser Asn Ser Gln Ser Ile Asn Asp
    1145                1150                1155

Asp Ile Val Arg Lys Glu Asp Tyr Ile Tyr Leu Asp Phe Phe Asn
    1160                1165                1170

Leu Asn Gln Glu Trp Arg Val Tyr Thr Tyr Lys Tyr Phe Lys Lys
    1175                1180                1185

Glu Glu Glu Lys Leu Phe Leu Ala Pro Ile Ser Asp Ser Asp Glu
    1190                1195                1200

Phe Tyr Asn Thr Ile Gln Ile Lys Glu Tyr Asp Glu Gln Pro Thr
    1205                1210                1215

Tyr Ser Cys Gln Leu Leu Phe Lys Lys Asp Glu Glu Ser Thr Asp
    1220                1225                1230

Glu Ile Gly Leu Ile Gly Ile His Arg Phe Tyr Glu Ser Gly Ile
    1235                1240                1245

Val Phe Glu Glu Tyr Lys Asp Tyr Phe Cys Ile Ser Lys Trp Tyr
    1250                1255                1260

Leu Lys Glu Val Lys Arg Lys Pro Tyr Asn Leu Lys Leu Gly Cys
    1265                1270                1275

Asn Trp Gln Phe Ile Pro Lys Asp Glu Gly Trp Thr Glu
    1280                1285                1290

<210> SEQ ID NO 5
<211> LENGTH: 3843
<212> TYPE: DNA
<213> ORGANISM: Clostridium botulinum

<400> SEQUENCE: 5
atgccaataa caattaacaa ctttaattat tcagatcctg ttgataataa aaatatttta      60
tatttagata ctcatttaaa tacattagct aatgagcctg aaaaagcctt tcgcattata     120
gggaatatat gggtaatacc cgatagattt tcaagagatt ctaatccaaa tttaaataaa     180
cctcctcgag ttacaagccc taaaagtggt tattatgatc ctaattattt gagtactgat     240
tctgaaaaag atacattttt aaaagaaatt ataaagttat ttaaagaat taactctaga     300
```

```
gaaataggag aagaattaat atatagactt gcaacagaca tacccttcc tgggaataac    360 aatactccaa ttaatacttt tgattttgat gtagatttta acagtgttga tgttaaaact    420
agacaaggta caactgggt taaaactggt agtataaatc ctagtgttat aataactgga    480
cctagagaaa acattataga cccagaaact tctacgttta aattaactaa caatactttt    540
gcggcacaag aaggatttgg tgctttatca ataatttcaa tatcacctag atttatgcta    600
acatatagta atgcaactaa taatgtagga gagggtagat tttctaagtc tgaattttgc    660
atggatccaa tactaatttt aatgcatgaa cttaatcatg caatgcataa tttatatgga    720
atagctatac caaatgatca aagaatttca tctgtaacta gtaatatttt ttattctcaa    780
tataaggtga aattagagta tgcagaaata tatgcatttg gaggtccaac tatagacctt    840
attcctaaaa gtgcaaggaa atattttgag gaaaaggcat tggattatta tagatccata    900
gctaaaagac ttaatagtat aactactgca aatccttcaa gctttaataa atatataggaa    960 gaatataaac agaaacttat tagaaagtat agattcgtag tagaatcttc aggtgaagtt   1020
gcagtagatc gtaataagtt tgctgagtta tataaagaac ttacacaaat atttacagaa   1080
tttaactacg ctaaaatata taatgtacaa aataggaaaa tatatctttc aaatgtatat   1140
actccggtta cggcaaatat attagacgat aatgttatg atatacaaaa tggatttaac   1200
atacctaaaa gtaatttaaa tgtactattt atgggtcaaa atttatctcg aaatccagca   1260
ttaagaaaag tcaatcctga aaatatgctt tatttattta caaattttg ccataaagca   1320 atagatggta gatcattata taataaaaca ttagattgta gagagctttt agttaaaaat   1380
actgacttac cctttatagg tgatattagt gatatcaaaa ctgatatatt tttaagcaaa   1440
gatattaatg aagaaactga agttatagac tatccggaca atgtttcagt ggatcaagtt   1500
attctcagta gaataccctc agaacatgga caactagatt tattatacc tattattgaa   1560 ggtgagagtc aagtattacc gggagagaat caagtctttt atgataatag aactcaaaat   1620
gttgattatt tgaattctta ttattaccta gaatctcaaa aactaagtga taatgttgaa   1680
gattttactt ttacgacatc aattgaggaa gctttggata atagtggaaa agtatatact   1740
tactttccta aactagctga taagtaaat acgggtgttc aaggtggttt atttttaatg   1800
tgggcaaatg atgtagttga agattttact acaaatattc taagaaaaga tacattagat   1860
aaaatatcag atgtatcagc tattattccc tatataggac ctgcattaaa tataagtaat   1920
tctgtaagaa ggggaaattt tactgaagca tttgcagtta ccggtgtaac tattttatta   1980 gaagcgttc aagaatttac aatacctgca cttggtgcat tgtgattta tagtaaggtt   2040 caagaaagaa acgagattat taaaactata gataattgtt tagaacaaag gattaaaaga   2100
tggaaagatt catatgaatg gatgatagga acgtggttat ccaggattac tactcaattt   2160
aataatataa gttatcaaat gtatgattct ttaaattatc aggcagatgc aatcaaagat   2220
aaaatagatt tagaatataa aaaatactca ggaagtgata agaaaatat aaaaagtcaa   2280 gttgaaaatt taaaaatag tttagatata aaaatctcgg aagcaatgaa taatataaat   2340 aaattatac gagaatgttc tgtaacatac ttatttaaaa atatgctccc taaagtaatt   2400
gatgaattaa ataagtttga tttaaaaact aaaacagaat taattaatct tatagatagt   2460
cataatatta ttctagttgg tgaagtagat agattaaaag caaagtaaa tgagagtttt   2520 gaaaatacaa tacccttaa tatttttca tatactaata attctttatt aaagatata   2580 attaatgaat atttcaatag tattaatgat tcaaaaattt tgagcttaca aaacaaaaaa   2640
aatgctttag tggatacatc aggatataat gcagaagtga ggctagaagg tgatgttcaa   2700
```

-continued

```
gttaatacga tatatacaaa tgattttaaa ttaagtagtt caggagataa aattatagta    2760
aatttaaata ataatatttt atatagcgct atttatgaga actctagtgt tagttttgg    2820 attaagatat ctaaagattt aactaattct cataatgaat atacaataat taatagtata   2880
aaacaaaatt ctgggtggaa attatgtatt aggaatggca atatagaatg gattttacaa   2940
gatattaata gaaagtataa aagtttaatt tttgattata gtgaatcatt aagtcataca   3000
ggatatacaa ataaatggtt ttttgttact ataactaata atataatggg gtatatgaaa   3060
ctttatataa atggagaatt aaagcagagt gaaagaattg aagatttaaa tgaggttaag   3120
ttagataaaa ccatagtatt tggaatagat gagaatatag atgagaatca gatgcttttgg  3180 attagagatt ttaatatttt ttctaaagaa ttaagcaatg aagatattaa tattgtatat   3240
gagggacaaa tattaagaaa tgttattaaa gattattggg gaaatccttt gaagtttgat   3300
acagaatatt atattattaa tgataattat atagataggt atatagcacc taaaagtaat   3360
atacttgtac ttgttcagta tccagataga tctaaattat atactggaaa tcctattact   3420
attaaatcag tatctgataa gaatccttat agtagaattt taaatggaga taatataatg   3480
tttcatatgt tatataatag tgggaaatat atgataataa gagatactga tacaatatat   3540
gcaatagaag gaagagagtg ttcaaaaaat tgtgtatatg cattaaaatt acagagtaat   3600
ttaggtaatt atggtatagg tatatttagt ataaaaaata ttgtatctca aaataaaat    3660 tgtagtcaaa ttttctctag ttttatgaaa aatacaatgc ttctagcaga tatatataaa   3720
ccttggagat tttcttttga aaatgcatac acgccagttg cagtaactaa ttatgagaca   3780
aaactattat caacttcatc tttttggaaa tttatttcta gggatccagg atgggtagag   3840
taa                                                                3843
```

```
<210> SEQ ID NO 6
<211> LENGTH: 1280
<212> TYPE: PRT
<213> ORGANISM: Clostridium botulinum

<400> SEQUENCE: 6

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Ile Gly Asn Ile Trp Val Ile Pro Asp
            35                  40                  45

Arg Phe Ser Arg Asp Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
                100                 105                 110

Asp Ile Pro Phe Pro Gly Asn Asn Asn Thr Pro Ile Asn Thr Phe Asp
            115                 120                 125

Phe Asp Val Asp Phe Asn Ser Val Asp Val Lys Thr Arg Gln Gly Asn
        130                 135                 140

Asn Trp Val Lys Thr Gly Ser Ile Asn Pro Ser Val Ile Ile Thr Gly
145                 150                 155                 160
```

-continued

```
Pro Arg Glu Asn Ile Ile Asp Pro Glu Thr Ser Thr Phe Lys Leu Thr
                165                 170                 175
Asn Asn Thr Phe Ala Ala Gln Glu Gly Phe Gly Ala Leu Ser Ile Ile
            180                 185                 190
Ser Ile Ser Pro Arg Phe Met Leu Thr Tyr Ser Asn Ala Thr Asn Asn
        195                 200                 205
Val Gly Glu Gly Arg Phe Ser Lys Ser Glu Phe Cys Met Asp Pro Ile
210                 215                 220
Leu Ile Leu Met His Glu Leu Asn His Ala Met His Asn Leu Tyr Gly
225                 230                 235                 240
Ile Ala Ile Pro Asn Asp Gln Arg Ile Ser Ser Val Thr Ser Asn Ile
                245                 250                 255
Phe Tyr Ser Gln Tyr Lys Val Lys Leu Glu Tyr Ala Glu Ile Tyr Ala
            260                 265                 270
Phe Gly Gly Pro Thr Ile Asp Leu Ile Pro Lys Ser Ala Arg Lys Tyr
        275                 280                 285
Phe Glu Glu Lys Ala Leu Asp Tyr Tyr Arg Ser Ile Ala Lys Arg Leu
290                 295                 300
Asn Ser Ile Thr Thr Ala Asn Pro Ser Ser Phe Asn Lys Tyr Ile Gly
305                 310                 315                 320
Glu Tyr Lys Gln Lys Leu Ile Arg Lys Tyr Arg Phe Val Val Glu Ser
                325                 330                 335
Ser Gly Glu Val Ala Val Asp Arg Asn Lys Phe Ala Glu Leu Tyr Lys
            340                 345                 350
Glu Leu Thr Gln Ile Phe Thr Glu Phe Asn Tyr Ala Lys Ile Tyr Asn
        355                 360                 365
Val Gln Asn Arg Lys Ile Tyr Leu Ser Asn Val Tyr Thr Pro Val Thr
370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
            420                 425                 430
Phe Thr Lys Phe Cys His Lys Ala Ile Asp Gly Arg Ser Leu Tyr Asn
        435                 440                 445
Lys Thr Leu Asp Cys Arg Glu Leu Leu Val Lys Asn Thr Asp Leu Pro
450                 455                 460
Phe Ile Gly Asp Ile Ser Asp Ile Lys Thr Asp Ile Phe Leu Ser Lys
465                 470                 475                 480
Asp Ile Asn Glu Glu Thr Glu Val Ile Asp Tyr Pro Asp Asn Val Ser
                485                 490                 495
Val Asp Gln Val Ile Leu Ser Lys Asn Thr Ser Glu His Gly Gln Leu
            500                 505                 510
Asp Leu Leu Tyr Pro Ile Ile Glu Gly Glu Ser Gln Val Leu Pro Gly
        515                 520                 525
Glu Asn Gln Val Phe Tyr Asp Asn Arg Thr Gln Asn Val Asp Tyr Leu
530                 535                 540
Asn Ser Tyr Tyr Tyr Leu Glu Ser Gln Lys Leu Ser Asp Asn Val Glu
545                 550                 555                 560
Asp Phe Thr Phe Thr Thr Ser Ile Glu Glu Ala Leu Asp Asn Ser Gly
                565                 570                 575
Lys Val Tyr Thr Tyr Phe Pro Lys Leu Ala Asp Lys Val Asn Thr Gly
```

```
            580                 585                 590
Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
            610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                    645                 650                 655

Thr Ile Leu Leu Glu Ala Phe Gln Glu Phe Thr Ile Pro Ala Leu Gly
                660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
            690                 695                 700

Tyr Glu Trp Met Ile Gly Thr Trp Leu Ser Arg Ile Thr Thr Gln Phe
705                 710                 715                 720

Asn Asn Ile Ser Tyr Gln Met Tyr Asp Ser Leu Asn Tyr Gln Ala Asp
                725                 730                 735

Ala Ile Lys Asp Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
            755                 760                 765

Asp Ile Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
                820                 825                 830

Lys Ala Lys Val Asn Glu Ser Phe Glu Asn Thr Ile Pro Phe Asn Ile
            835                 840                 845

Phe Ser Tyr Thr Asn Asn Ser Leu Leu Lys Asp Ile Ile Asn Glu Tyr
850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
                900                 905                 910

Ser Ser Gly Asp Lys Ile Ile Val Asn Leu Asn Asn Asn Ile Leu Tyr
            915                 920                 925

Ser Ala Ile Tyr Glu Asn Ser Ser Val Ser Phe Trp Ile Lys Ile Ser
            930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
                980                 985                 990

Tyr Ser Glu Ser Leu Ser His Thr Gly Tyr Thr Asn Lys Trp Phe Phe
            995                 1000                1005
```

| Val | Thr | Ile | Thr | Asn | Asn | Ile | Met | Gly | Tyr | Met | Lys | Leu | Tyr | Ile |
|  | 1010 |  |  |  | 1015 |  |  |  |  | 1020 |  |  |  |  |

| Asn | Gly | Glu | Leu | Lys | Gln | Ser | Glu | Arg | Ile | Glu | Asp | Leu | Asn | Glu |
| 1025 |  |  |  |  | 1030 |  |  |  |  | 1035 |  |  |  |  |

| Val | Lys | Leu | Asp | Lys | Thr | Ile | Val | Phe | Gly | Ile | Asp | Glu | Asn | Ile |
| 1040 |  |  |  |  | 1045 |  |  |  |  | 1050 |  |  |  |  |

| Asp | Glu | Asn | Gln | Met | Leu | Trp | Ile | Arg | Asp | Phe | Asn | Ile | Phe | Ser |
| 1055 |  |  |  |  | 1060 |  |  |  |  | 1065 |  |  |  |  |

| Lys | Glu | Leu | Ser | Asn | Glu | Asp | Ile | Asn | Ile | Val | Tyr | Glu | Gly | Gln |
| 1070 |  |  |  |  | 1075 |  |  |  |  | 1080 |  |  |  |  |

| Ile | Leu | Arg | Asn | Val | Ile | Lys | Asp | Tyr | Trp | Gly | Asn | Pro | Leu | Lys |
| 1085 |  |  |  |  | 1090 |  |  |  |  | 1095 |  |  |  |  |

| Phe | Asp | Thr | Glu | Tyr | Tyr | Ile | Ile | Asn | Asp | Asn | Tyr | Ile | Asp | Arg |
| 1100 |  |  |  |  | 1105 |  |  |  |  | 1110 |  |  |  |  |

| Tyr | Ile | Ala | Pro | Lys | Ser | Asn | Ile | Leu | Val | Leu | Val | Gln | Tyr | Pro |
| 1115 |  |  |  |  | 1120 |  |  |  |  | 1125 |  |  |  |  |

| Asp | Arg | Ser | Lys | Leu | Tyr | Thr | Gly | Asn | Pro | Ile | Thr | Ile | Lys | Ser |
| 1130 |  |  |  |  | 1135 |  |  |  |  | 1140 |  |  |  |  |

| Val | Ser | Asp | Lys | Asn | Pro | Tyr | Ser | Arg | Ile | Leu | Asn | Gly | Asp | Asn |
| 1145 |  |  |  |  | 1150 |  |  |  |  | 1155 |  |  |  |  |

| Ile | Met | Phe | His | Met | Leu | Tyr | Asn | Ser | Gly | Lys | Tyr | Met | Ile | Ile |
| 1160 |  |  |  |  | 1165 |  |  |  |  | 1170 |  |  |  |  |

| Arg | Asp | Thr | Asp | Thr | Ile | Tyr | Ala | Ile | Glu | Gly | Arg | Glu | Cys | Ser |
| 1175 |  |  |  |  | 1180 |  |  |  |  | 1185 |  |  |  |  |

| Lys | Asn | Cys | Val | Tyr | Ala | Leu | Lys | Leu | Gln | Ser | Asn | Leu | Gly | Asn |
| 1190 |  |  |  |  | 1195 |  |  |  |  | 1200 |  |  |  |  |

| Tyr | Gly | Ile | Gly | Ile | Phe | Ser | Ile | Lys | Asn | Ile | Val | Ser | Gln | Asn |
| 1205 |  |  |  |  | 1210 |  |  |  |  | 1215 |  |  |  |  |

| Lys | Tyr | Cys | Ser | Gln | Ile | Phe | Ser | Ser | Phe | Met | Lys | Asn | Thr | Met |
| 1220 |  |  |  |  | 1225 |  |  |  |  | 1230 |  |  |  |  |

| Leu | Leu | Ala | Asp | Ile | Tyr | Lys | Pro | Trp | Arg | Phe | Ser | Phe | Glu | Asn |
| 1235 |  |  |  |  | 1240 |  |  |  |  | 1245 |  |  |  |  |

| Ala | Tyr | Thr | Pro | Val | Ala | Val | Thr | Asn | Tyr | Glu | Thr | Lys | Leu | Leu |
| 1250 |  |  |  |  | 1255 |  |  |  |  | 1260 |  |  |  |  |

| Ser | Thr | Ser | Ser | Phe | Trp | Lys | Phe | Ile | Ser | Arg | Asp | Pro | Gly | Trp |
| 1265 |  |  |  |  | 1270 |  |  |  |  | 1275 |  |  |  |  |

| Val | Glu |
| 1280 |  |

<210> SEQ ID NO 7
<211> LENGTH: 3858
<212> TYPE: DNA
<213> ORGANISM: Clostridium botulinum

<400> SEQUENCE: 7

```
atgacatggc cagtaaaaga tttaattat agtgatcctg ttaatgacaa tgatatatta    60
tatttaagaa taccacaaaa taagttaatt actacacctg taaaagcttt tatgattact   120
caaaatattt gggtaatacc agaaagattt catcagata ctaatccaag tttaagtaaa    180
ccgcctagac ctacttcaaa gtatcaaagt tattatgatc ctagttattt atctactgat   240
gagcaaaaag atacattttt aaagggatt ataaaattat ttaaagaat taatgaaaga   300
gatataggaa aaaattaat aaattattta gtagttggtt cacctttat gggagattca    360
agtacgcctg aagatacatt tgattttaca cgtcatacta ctaatattgc agttgaaaag   420
```

```
tttgaaaatg gtagttggaa agtaacaaat attataacac caagtgtatt gatatttgga      480
ccacttccta atatattaga ctatacagca tcccttacat tgcaaggaca acaatcaaat      540
ccatcatttg aagggtttgg aacattatct atactaaaag tagcacctga attttttgtta    600 acatttagtg atgtaacatc taatcaaagt tcagctgtat taggcaaatc tatattttgt     660
atggatccag taatagcttt aatgcatgag ttaacacatt ctttgcatca attgtatgga     720
ataaatatac catctgataa aaggattcgt ccacaagtta gcgagggatt tttttctcaa      780
gatggaccca acgtacaatt tgaggaatta tacacatttg gaggatcaga tgttgaaata     840
atacctcaaa ttgaaagatt acaattaaga gaaaaagcat taggtcacta taagatata      900 gcgaaaagac ttaataatat taataaaact attccttcta gttggagtag taatatagat     960
aaatataaaa aaatattttc tgaaaagtat aattttgata agataatac aggaaatttt      1020 gttgtaaata ttgataaatt caatagctta tattcagact tgactaatgt tatgtcagaa     1080
gttgtttatt cttcgcaata taatgttaaa aacaggactc attattttc aaagcattat      1140 ctacctgtat ttgcaaatat attagatgat aatatttata ctataataaa cggttttaat    1200
ttaacaacta aaggttttaa tatagaaaat tcgggtcaga atatagaaag gaatcctgca     1260
ctacaaaaac ttagttcaga aagtgtagta gatttgttta caaagtatg tttaagatta      1320 acaagaaata gtagagatga ttcaacatgt attcaagtta aaaataatac attaccttat     1380
gtagctgata aagatagcat ttcacaagaa atatttgaaa gtcaaattat tacagatgag    1440
actaatgtag aaaattattc agataatttt tcattagatg aatctatttt agatgcaaaa     1500
gtccctacta atcctgaagc agtagatcca ctgttaccca atgttaatat ggaaccttta     1560
aatgttccag gtgaagaaga agtatttta tgatgatatta ctaaagatgt tgattattta    1620
aactcttatt attatttgga agcccaaaaa ttaagtaata atgttgaaaa tattactctt    1680
acaacttcag ttgaagaagc attaggttat agcaataaga tatacacatt tttacctagc    1740
ttagctgaaa aagtgaataa aggtgttcaa gcaggtttat tcttaaattg ggcgaatgaa    1800
gtagttgagg atttttactac aaatattatg aaaaaagata cattggataa atatatcagat  1860 gtatcagcca taattccata tataggacct gccttaaata taggaaattc agcattaagg    1920
ggaaacttta agcaagcatt tgcaacagct ggtgtagctt ttttgttaga aggattttcca   1980 gagtttacaa tacctgcact cggtgtattt acctttttata gttctattca agaaagagag   2040
aaaattatta aaactataga aaattgttta gaacaaagag ttaagagatg gaaagattca    2100
tatcaatgga tggtatcaaa ttggttgtca agaattacta ctcgatttaa tcatataagt    2160
tatcaaatgt atgattcttt gagttatcag gcagatgcaa tcaaagctaa aatagattta   2220
gaatataaaa aatactcagg aagtgataaa gaaaatataa aaagtcaagt tgaaaattta   2280
aaaaatagtt tagatgtaaa aatctcggaa gcaatgaata atataaataa atttatacga   2340
gaatgttctg taacatactt atttaaaaat atgctcccta agtaattga tgaattaaat    2400 aagtttgatt taaaaactaa aacagaatta attaatctta tagatagtca taatattatt    2460
ctagttggtg aagtagatag attaaaagca aaagtaaatg agagttttga aaatacaata    2520
ccctttaata tttttttcata tactaataat tctttattaa aagatatgat taatgaatat    2580
ttcaatagta ttaatgattc aaaaattttg agcttacaaa ataaaaaaaa tactttgatg    2640
gatacatcag gatataacgc agaagtgaga gtagaaggca atgttcagct taatccaata    2700
tttccatttg actttaaatt aggtagttca ggggatgata gaggtaaagt tatagtaacc    2760
```

```
cagaatgaaa atattgtata taatgctatg tatgaaagtt ttagtattag tttttggatt    2820
aggataaata aatgggtaag taatttacct ggatatacta taattgatag tgttaaaaat    2880
aactcaggtt ggagtatagg tattattagt aattttttag tgtttacttt aaaacaaaat    2940
gaaaatagtg aacaagatat aaactttagt tatgatatat caaagaatgc tgcgggatat    3000
aataaatggt ttttgtaac tattactacc aatatgatgg gaaatatgat gatttatata    3060
aatggaaaat taatagatac tataaaagtt aaagagttaa ctggaattaa ttttagcaaa    3120
actataacat ttcaaatgaa taaaattcca aatactggct taattacctc agattctgat    3180
aacatcaata tgtggataag ggattttat atctttgcta aagaattaga tgataaagat    3240
attaatatat tatttaatag cttgcaatat actaatgttg taaaagatta ttggggaaat    3300
gatttaagat atgataaaga atattacatg attaacgtaa attatatgaa tagatatatg    3360
tctaaaaaag gcaatggaat tgttttttaat acacgtaaaa ataataatga cttcaatgaa    3420
ggatataaaa ttataataaa aagaattaga ggaaatacaa atgatactag agtacgagga    3480
gaaaatgtat tatattttaa tactacaatt gataacaaac aatatagttt aggtatgtat    3540
aaaccttcta gaaatctagg gactgattta gttccactag gtgcattgga tcaaccaatg    3600
gatgagatac gtaaatatgg ttcgtttata atacaaccat gcaatacttt tgattactat    3660
gcatcacaat tattttttgtc aagtaatgca acaacaaata ggcttggaat actatcaatt    3720
ggtagttata gtttcaaact tggagatgac tattggttta atcacgaata tttaattcct    3780
gttataaaaa tagagcatta tgcttcatta ttagaatcaa catcaactca ttgggttttt    3840
gtacctgcaa gtgaataa                                                 3858
```

<210> SEQ ID NO 8
<211> LENGTH: 1285
<212> TYPE: PRT
<213> ORGANISM: Clostridium botulinum

<400> SEQUENCE: 8

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175
```

```
Gln Gln Ser Asn Pro Ser Phe Glu Gly Phe Gly Thr Leu Ser Ile Leu
                180                 185                 190
Lys Val Ala Pro Glu Phe Leu Leu Thr Phe Ser Asp Val Thr Ser Asn
            195                 200                 205
Gln Ser Ser Ala Val Leu Gly Lys Ser Ile Phe Cys Met Asp Pro Val
        210                 215                 220
Ile Ala Leu Met His Glu Leu Thr His Ser Leu His Gln Leu Tyr Gly
225                 230                 235                 240
Ile Asn Ile Pro Ser Asp Lys Arg Ile Arg Pro Gln Val Ser Glu Gly
                245                 250                 255
Phe Phe Ser Gln Asp Gly Pro Asn Val Gln Phe Glu Glu Leu Tyr Thr
            260                 265                 270
Phe Gly Gly Ser Asp Val Glu Ile Ile Pro Gln Ile Glu Arg Leu Gln
        275                 280                 285
Leu Arg Glu Lys Ala Leu Gly His Tyr Lys Asp Ile Ala Lys Arg Leu
290                 295                 300
Asn Asn Ile Asn Lys Thr Ile Pro Ser Ser Trp Ser Ser Asn Ile Asp
305                 310                 315                 320
Lys Tyr Lys Lys Ile Phe Ser Glu Lys Tyr Asn Phe Asp Lys Asp Asn
                325                 330                 335
Thr Gly Asn Phe Val Val Asn Ile Asp Lys Phe Asn Ser Leu Tyr Ser
            340                 345                 350
Asp Leu Thr Asn Val Met Ser Glu Val Val Tyr Ser Ser Gln Tyr Asn
        355                 360                 365
Val Lys Asn Arg Thr His Tyr Phe Ser Lys His Tyr Leu Pro Val Phe
370                 375                 380
Ala Asn Ile Leu Asp Asp Asn Ile Tyr Thr Ile Ile Asn Gly Phe Asn
385                 390                 395                 400
Leu Thr Thr Lys Gly Phe Asn Ile Glu Asn Ser Gly Gln Asn Ile Glu
                405                 410                 415
Arg Asn Pro Ala Leu Gln Lys Leu Ser Ser Glu Ser Val Val Asp Leu
            420                 425                 430
Phe Thr Lys Val Cys Leu Arg Leu Thr Arg Asn Ser Arg Asp Asp Ser
        435                 440                 445
Thr Cys Ile Gln Val Lys Asn Asn Thr Leu Pro Tyr Val Ala Asp Lys
450                 455                 460
Asp Ser Ile Ser Gln Glu Ile Phe Glu Ser Gln Ile Ile Thr Asp Glu
465                 470                 475                 480
Thr Asn Val Glu Asn Tyr Ser Asp Asn Phe Ser Leu Asp Glu Ser Ile
                485                 490                 495
Leu Asp Ala Lys Val Pro Thr Asn Pro Glu Ala Val Asp Pro Leu Leu
            500                 505                 510
Pro Asn Val Asn Met Glu Pro Leu Asn Val Pro Gly Glu Glu Glu Val
        515                 520                 525
Phe Tyr Asp Asp Ile Thr Lys Asp Val Asp Tyr Leu Asn Ser Tyr Tyr
530                 535                 540
Tyr Leu Glu Ala Gln Lys Leu Ser Asn Asn Val Glu Asn Ile Thr Leu
545                 550                 555                 560
Thr Thr Ser Val Glu Glu Ala Leu Gly Tyr Ser Asn Lys Ile Tyr Thr
                565                 570                 575
Phe Leu Pro Ser Leu Ala Glu Lys Val Asn Lys Gly Val Gln Ala Gly
            580                 585                 590
Leu Phe Leu Asn Trp Ala Asn Glu Val Val Glu Asp Phe Thr Thr Asn
```

-continued

```
                595                 600                 605
Ile Met Lys Lys Asp Thr Leu Asp Lys Ile Ser Asp Val Ser Ala Ile
610                 615                 620
Ile Pro Tyr Ile Gly Pro Ala Leu Asn Ile Gly Asn Ser Ala Leu Arg
625                 630                 635                 640
Gly Asn Phe Lys Gln Ala Phe Ala Thr Ala Gly Val Ala Phe Leu Leu
            645                 650                 655
Glu Gly Phe Pro Glu Phe Thr Ile Pro Ala Leu Gly Val Phe Thr Phe
            660                 665                 670
Tyr Ser Ser Ile Gln Glu Arg Glu Lys Ile Ile Lys Thr Ile Glu Asn
            675                 680                 685
Cys Leu Glu Gln Arg Val Lys Arg Trp Lys Asp Ser Tyr Gln Trp Met
690                 695                 700
Val Ser Asn Trp Leu Ser Arg Ile Thr Thr Arg Phe Asn His Ile Ser
705                 710                 715                 720
Tyr Gln Met Tyr Asp Ser Leu Ser Tyr Gln Ala Asp Ala Ile Lys Ala
            725                 730                 735
Lys Ile Asp Leu Glu Tyr Lys Lys Tyr Ser Gly Ser Asp Lys Glu Asn
            740                 745                 750
Ile Lys Ser Gln Val Glu Asn Leu Lys Asn Ser Leu Asp Val Lys Ile
            755                 760                 765
Ser Glu Ala Met Asn Asn Ile Asn Lys Phe Ile Arg Glu Cys Ser Val
770                 775                 780
Thr Tyr Leu Phe Lys Asn Met Leu Pro Lys Val Ile Asp Glu Leu Asn
785                 790                 795                 800
Lys Phe Asp Leu Lys Thr Lys Thr Glu Leu Ile Asn Leu Ile Asp Ser
            805                 810                 815
His Asn Ile Ile Leu Val Gly Glu Val Asp Arg Leu Lys Ala Lys Val
            820                 825                 830
Asn Glu Ser Phe Glu Asn Thr Ile Pro Phe Asn Ile Phe Ser Tyr Thr
            835                 840                 845
Asn Asn Ser Leu Leu Lys Asp Met Ile Asn Glu Tyr Phe Asn Ser Ile
850                 855                 860
Asn Asp Ser Lys Ile Leu Ser Leu Gln Asn Lys Lys Asn Thr Leu Met
865                 870                 875                 880
Asp Thr Ser Gly Tyr Asn Ala Glu Val Arg Val Glu Gly Asn Val Gln
            885                 890                 895
Leu Asn Pro Ile Phe Pro Phe Asp Phe Lys Leu Gly Ser Ser Gly Asp
            900                 905                 910
Asp Arg Gly Lys Val Ile Val Thr Gln Asn Glu Asn Ile Val Tyr Asn
            915                 920                 925
Ala Met Tyr Glu Ser Phe Ser Ile Ser Phe Trp Ile Arg Ile Asn Lys
            930                 935                 940
Trp Val Ser Asn Leu Pro Gly Tyr Thr Ile Ile Asp Ser Val Lys Asn
945                 950                 955                 960
Asn Ser Gly Trp Ser Ile Gly Ile Ile Ser Asn Phe Leu Val Phe Thr
            965                 970                 975
Leu Lys Gln Asn Glu Asn Ser Glu Gln Asp Ile Asn Phe Ser Tyr Asp
            980                 985                 990
Ile Ser Lys Asn Ala Ala Gly Tyr  Asn Lys Trp Phe Phe Val Thr Ile
            995                 1000                1005
Thr Thr  Asn Met Met Gly Asn  Met Met Ile Tyr Ile  Asn Gly Lys
            1010                1015                1020
```

```
Leu Ile Asp Thr Ile Lys Val Lys Glu Leu Thr Gly Ile Asn Phe
    1025                1030                1035

Ser Lys Thr Ile Thr Phe Gln Met Asn Lys Ile Pro Asn Thr Gly
    1040                1045                1050

Leu Ile Thr Ser Asp Ser Asp Asn Ile Asn Met Trp Ile Arg Asp
    1055                1060                1065

Phe Tyr Ile Phe Ala Lys Glu Leu Asp Asp Lys Asp Ile Asn Ile
    1070                1075                1080

Leu Phe Asn Ser Leu Gln Tyr Thr Asn Val Val Lys Asp Tyr Trp
    1085                1090                1095

Gly Asn Asp Leu Arg Tyr Asp Lys Glu Tyr Tyr Met Ile Asn Val
    1100                1105                1110

Asn Tyr Met Asn Arg Tyr Met Ser Lys Lys Gly Asn Gly Ile Val
    1115                1120                1125

Phe Asn Thr Arg Lys Asn Asn Asn Asp Phe Asn Glu Gly Tyr Lys
    1130                1135                1140

Ile Ile Ile Lys Arg Ile Arg Gly Asn Thr Asn Asp Thr Arg Val
    1145                1150                1155

Arg Gly Glu Asn Val Leu Tyr Phe Asn Thr Thr Ile Asp Asn Lys
    1160                1165                1170

Gln Tyr Ser Leu Gly Met Tyr Lys Pro Ser Arg Asn Leu Gly Thr
    1175                1180                1185

Asp Leu Val Pro Leu Gly Ala Leu Asp Gln Pro Met Asp Glu Ile
    1190                1195                1200

Arg Lys Tyr Gly Ser Phe Ile Ile Gln Pro Cys Asn Thr Phe Asp
    1205                1210                1215

Tyr Tyr Ala Ser Gln Leu Phe Leu Ser Ser Asn Ala Thr Thr Asn
    1220                1225                1230

Arg Leu Gly Ile Leu Ser Ile Gly Ser Tyr Ser Phe Lys Leu Gly
    1235                1240                1245

Asp Asp Tyr Trp Phe Asn His Glu Tyr Leu Ile Pro Val Ile Lys
    1250                1255                1260

Ile Glu His Tyr Ala Ser Leu Leu Glu Ser Thr Ser Thr His Trp
    1265                1270                1275

Val Phe Val Pro Ala Ser Glu
    1280                1285

<210> SEQ ID NO 9
<211> LENGTH: 3756
<212> TYPE: DNA
<213> ORGANISM: Clostridium botulinum

<400> SEQUENCE: 9
atgccaaaaa ttaatagttt taattataat gatcctgtta atgatagaac aattttatat    60
attaaaccag gcggttgtca agaattttat aaatcattta atattatgaa aaatatttgg   120
ataattccag agagaaatgt aattggtaca accccccaag attttcatcc gcctacttca   180
ttaaaaaatg gagatagtag ttattatgac cctaattatt tacaaagtga tgaagaaaag   240
gatagatttt taaaaatagt cacaaaaata tttaatagaa taataataa tctttcagga   300 gggattttat tagaagaact gtcaaaagct aatccatatt tagggaatga taatactcca   360
gataatcaat tccatattgg tgatgcatca gcagttgaga ttaaattctc aaatggtagc   420
caagacatac tattacctaa tgttattata atgggagcag agcctgattt atttgaaact   480
```

```
aacagttcca atatttctct aagaaataat tatatgccaa gcaatcaccg tttggatca    540 atagctatag taacattctc acctgaatat tcttttagat ttaatgataa ttgtatgaat    600
gaatttattc aagatcctgc tcttacatta atgcatgaat taatacattc attacatgga    660
ctatatgggg ctaaagggat tactacaaag tatactataa cacaaaaaca aaatccccta    720
ataacaaata taagaggtac aaatattgaa gaattcttaa cttttggagg tactgattta    780
aacattatta ctagtgctca gtccaatgat atctatacta atcttctagc tgattataaa    840
aaaatagcgt ctaaacttag caaagtacaa gtatctaatc cactacttaa tccttataaa    900 gatgttttg aagcaaagta tggattagat aaagatgcta gcggaattta ttcggtaaat    960
ataaacaaat ttaatgatat ttttaaaaaa ttatacagct ttacggaatt tgatttacga   1020
actaaatttc aagttaaatg taggcaaact tatattggac agtataaata cttcaaactt   1080
tcaaacttgt taaatgattc tatttataat atatcagaag gctataatat aaataattta   1140
aaggtaaatt ttagaggaca gaatgcaaat ttaaatccta gaattattac accaattaca   1200
ggtagaggac tagtaaaaaa aatcattaga ttttgtaaaa atattgtttc tgtaaaaggc   1260
ataaggaaat caatatgtat cgaaataaat aatggtgagt tatttttttgt ggcttccgag   1320 aatagttata atgatgataa tataaatact cctaaagaaa ttgacgatac agtaacttca   1380
aataataatt atgaaaatga tttagatcag gttattttaa attttaatag tgaatcagca   1440
cctggacttt cagatgaaaa attaaattta actatccaaa atgatgctta tacccaaaa    1500 tatgattcta atggaacaag tgatatagaa caacatgatg ttaatgaact taatgtatttt   1560 ttctatttag atgcacagaa agtgcccgaa ggtgaaaata atgtcaatct cacctcttca   1620
attgatacag cattattaga acaacctaaa atatatacat ttttttcatc agaatttatt   1680
aataatgtca ataaacctgt gcaagcagca ttatttgtaa gctggataca acaagtgtta   1740 gtagattta ctactgaagc taaccaaaaa agtactgttg ataaaattgc agatatttct   1800
atagttgttc catatatagg tcttgcttta aatataggaa atgaagcaca aaaaggaaat   1860
tttaaagatg cacttgaatt attaggagca ggtatttat tagaatttga acccgagctt   1920
ttaattccta caattttagt attcacgata aaatcttttt taggttcatc tgataataaa   1980
aataaagtta ttaaagcaat aaataatgca ttgaaagaaa gagatgaaaa atggaaagaa   2040
gtatatagtt ttatagtatc gaattggatg actaaaatta atacacaatt taataaaaga   2100
aaagaacaaa tgtatcaagc tttacaaaat caagtaaatg caattaaaac aataatagaa   2160
tctaagtata atagttatac tttagaggaa aaaaatgagc ttacaaataa atatgatatt   2220
aagcaaatag aaaatgaact taatcaaaag gtttctatag caatgaataa tatagacagg   2280
ttcttaactg aaagttctat atcctattta atgaaaataa taaatgaagt aaaaattaat   2340
aaattaagag aatatgatga gaatgtcaaa acgtatttat tgaattatat tatacaacat   2400
ggatcaatct tgggagagag tcagcaagaa ctaaattcta tggtaactga tacccctaaat   2460 aatagtattc cttttaagct ttcttcttat acagatgata aaattttaat ttcatatttt   2520
aataaattct taagagaat taaaagtagt tcagttttaa atatgagata taaaaatgat   2580
aaatacgtag atacttcagg atatgattca aatataaata ttaatggaga tgtatataaa   2640
tatccaacta ataaaaatca atttggaata tataatgata aacttagtga agttaatata   2700
tctcaaaatg attacattat atatgataat aaatataaaa attttagtat tagttttttgg   2760 gtaagaattc ctaactatga taataagata gtaaatgtta ataatgaata cactataata   2820
aattgtatga gagataataa ttcaggatgg aaagtatctc ttaatcataa tgaaataatt   2880
```

```
tggacattcg aagataatcg aggaattaat caaaaattag catttaacta tggtaacgca    2940
aatggtattt ctgattatat aaataagtgg attttgtaa ctataactaa tgatagatta    3000
ggagattcta aactttatat taatggaaat ttaatagatc aaaaatcaat tttaaattta    3060
ggtaatattc atgttagtga caatatatta tttaaaatag ttaattgtag ttatacaaga    3120
tatattggta ttagatattt taatattttt gataaagaat tagatgaaac agaaattcaa    3180
actttatata gcaatgaacc taatacaaat attttgaagg attttggggg aaattatttg    3240
ctttatgaca agaatacta tttattaaat gtgttaaaac caaataactt tattgatagg    3300
agaaaagatt ctactttaag cattaataat ataagaagca ctattctttt agctaataga    3360
ttatatagtg aataaaagt taaaatacaa agagttaata atagtagtac taacgataat    3420
cttgttagaa agaatgatca ggtatatatt aattttgtag ccagcaaaac tcacttattt    3480
ccattatatg ctgatacagc taccacaaat aaagagaaaa caataaaaat atcatcatct    3540
ggcaatagat ttaatcaagt agtagttatg aattcagtag gaaattgtac aatgaatttt    3600
aaaaataata atggaaataa tattgggttg ttaggtttca aggcagatac tgtcgttgct    3660
agtacttggt attatacaca tatgagagat catacaaaca gcaatggatg ttttttggaac   3720 tttatttctg aagaacatgg atggcaagaa aaataa                              3756

<210> SEQ ID NO 10
<211> LENGTH: 1251
<212> TYPE: PRT
<213> ORGANISM: Clostridium botulinum

<400> SEQUENCE: 10

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
```

```
            210                 215                 220
Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                    245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
        290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                    325                 330                 335

Phe Asp Leu Arg Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Asn Asn Leu Lys Val Asn Phe
        370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                    405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
        450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                    485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
        530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                    565                 570                 575

Gln Gln Val Leu Val Asp Phe Thr Thr Glu Ala Asn Gln Lys Ser Thr
                580                 585                 590

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
        610                 615                 620

Leu Glu Leu Leu Gly Ala Gly Ile Leu Leu Glu Phe Glu Pro Glu Leu
625                 630                 635                 640
```

```
Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Ile Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Lys Arg Ile Lys
        835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn  Leu Ile Asp Gln Lys  Ser Ile Leu Asn Leu  Gly Asn Ile
    1010                1015                1020

His Val  Ser Asp Asn Ile Leu  Phe Lys Ile Val Asn  Cys Ser Tyr
    1025                1030                1035

Thr Arg  Tyr Ile Gly Ile Arg  Tyr Phe Asn Ile Phe  Asp Lys Glu
    1040                1045                1050
```

| Leu | Asp | Glu | Thr | Glu | Ile | Gln | Thr | Leu | Tyr | Ser | Asn | Glu | Pro | Asn |
|---|---|---|---|---|---|---|---|---|---|---|---|---|---|---|
| 1055 | | | | | 1060 | | | | | 1065 | | | | |

| Thr | Asn | Ile | Leu | Lys | Asp | Phe | Trp | Gly | Asn | Tyr | Leu | Leu | Tyr | Asp |
|---|---|---|---|---|---|---|---|---|---|---|---|---|---|---|
| 1070 | | | | | 1075 | | | | | 1080 | | | | |

| Lys | Glu | Tyr | Tyr | Leu | Leu | Asn | Val | Leu | Lys | Pro | Asn | Asn | Phe | Ile |
|---|---|---|---|---|---|---|---|---|---|---|---|---|---|---|
| 1085 | | | | | 1090 | | | | | 1095 | | | | |

| Asp | Arg | Arg | Lys | Asp | Ser | Thr | Leu | Ser | Ile | Asn | Asn | Ile | Arg | Ser |
|---|---|---|---|---|---|---|---|---|---|---|---|---|---|---|
| 1100 | | | | | 1105 | | | | | 1110 | | | | |

| Thr | Ile | Leu | Leu | Ala | Asn | Arg | Leu | Tyr | Ser | Gly | Ile | Lys | Val | Lys |
|---|---|---|---|---|---|---|---|---|---|---|---|---|---|---|
| 1115 | | | | | 1120 | | | | | 1125 | | | | |

| Ile | Gln | Arg | Val | Asn | Asn | Ser | Ser | Thr | Asn | Asp | Asn | Leu | Val | Arg |
|---|---|---|---|---|---|---|---|---|---|---|---|---|---|---|
| 1130 | | | | | 1135 | | | | | 1140 | | | | |

| Lys | Asn | Asp | Gln | Val | Tyr | Ile | Asn | Phe | Val | Ala | Ser | Lys | Thr | His |
|---|---|---|---|---|---|---|---|---|---|---|---|---|---|---|
| 1145 | | | | | 1150 | | | | | 1155 | | | | |

| Leu | Phe | Pro | Leu | Tyr | Ala | Asp | Thr | Ala | Thr | Thr | Asn | Lys | Glu | Lys |
|---|---|---|---|---|---|---|---|---|---|---|---|---|---|---|
| 1160 | | | | | 1165 | | | | | 1170 | | | | |

| Thr | Ile | Lys | Ile | Ser | Ser | Ser | Gly | Asn | Arg | Phe | Asn | Gln | Val | Val |
|---|---|---|---|---|---|---|---|---|---|---|---|---|---|---|
| 1175 | | | | | 1180 | | | | | 1185 | | | | |

| Val | Met | Asn | Ser | Val | Gly | Asn | Cys | Thr | Met | Asn | Phe | Lys | Asn | Asn |
|---|---|---|---|---|---|---|---|---|---|---|---|---|---|---|
| 1190 | | | | | 1195 | | | | | 1200 | | | | |

| Asn | Gly | Asn | Asn | Ile | Gly | Leu | Leu | Gly | Phe | Lys | Ala | Asp | Thr | Val |
|---|---|---|---|---|---|---|---|---|---|---|---|---|---|---|
| 1205 | | | | | 1210 | | | | | 1215 | | | | |

| Val | Ala | Ser | Thr | Trp | Tyr | Tyr | Thr | His | Met | Arg | Asp | His | Thr | Asn |
|---|---|---|---|---|---|---|---|---|---|---|---|---|---|---|
| 1220 | | | | | 1225 | | | | | 1230 | | | | |

| Ser | Asn | Gly | Cys | Phe | Trp | Asn | Phe | Ile | Ser | Glu | Glu | His | Gly | Trp |
|---|---|---|---|---|---|---|---|---|---|---|---|---|---|---|
| 1235 | | | | | 1240 | | | | | 1245 | | | | |

| Gln | Glu | Lys |
|---|---|---|
| 1250 | | |

<210> SEQ ID NO 11
<211> LENGTH: 3843
<212> TYPE: DNA
<213> ORGANISM: Clostridium botulinum

<400> SEQUENCE: 11

```
atgccagttg taataaatag ttttaattat aatgaccctg ttaatgatga acaatttta      60
tacatgcaga aaccatatga agaaagaagt agaaaatatt ataaagcttt tgagattatg     120
cctaatgttt ggataatgcc tgagagagat acaataggaa ctaagcctga tgagtttcag     180
gtgccggatt cattaaagaa cggaagtagt gcttattatg atcctaatta tttaaccact     240
gatgctgaaa aagatagata tttaaaaaca atgataaaat tatttaatag aattaatagt     300
aatcctacag ggaaagtttt gttagaagaa gtatcaaatg ctagaccata tttaggagat     360
gatgacacgc taattaatga attccttcca gttaatgtaa ctacaagtgt taatataaaa     420
ttttcaactg atgttgaaag ttcaataata tcgaatcttc ttgtattggg agcaggacct     480
gatatattta agcttactg tacccccctt gtaaggttta taagtcaga taaattaatt     540
gaaccaagta atcatggttt tggatcaatt aatatcttga cattttcacc tgagtatgaa     600
catatttta atgatattag tggagggaat cataatagta cagaatcatt tattgcagat     660
cctgcaattt cactagctca tgaattgata catgcactac atggattata cggggctaag     720
gcagttactc ataagagtc tctagtagca gagcgaggac ctcttatgat agccgaaaag     780
cccataaggc tagaagaatt tttaactttt ggaggtgagg atttaaatat cattcctagt     840
gctatgaagg aaaaaatata taacgatctt ttagctaact atgaaaaaat agctactaga     900
```

```
cttagagaag ttaatacggc tcctcctgga tatgatatta atgaatataa agattatttt    960
caatggaagt atggactaga tagaaatgca gatggaagtt atactgtgaa tagaaataaa   1020
tttaatgaaa tttataaaaa attatatagc tttacagaga ttgacttagc aaataaattt   1080
aaagtaaaat gtagaaatac ttattttatt aaatatggat ttgtaaaagt tccaaatttg   1140
ttagatgatg atatttatac tgtatcagag gggtttaata taggtaattt agcagtaaac   1200
aatcgcggac aaaatataaa tttaaatcct aaaattattg attccattcc agataaaggt   1260
ttagtggaaa agattattaa attttgtaag agcattattc ctagaaaagg tacgaagcag   1320
tcaccgtcac tatgcattag agtaaataat agggagttat tttttgtagc ttcagaaagt   1380
agctataatg aaagtgatat taatacacct aaagaaattg acgatacaac aaatctaaat   1440
aataattata gaataatttt agatgaagtt attttagatt ataatagtga gacaatacct   1500
caaatatcaa atcgaacatt aaatacactt gtacaagaca atagttatgt gccaagatat   1560
gattctaatg gaacaagtga aatagaggaa tatgatgttg ttgactttaa tgtatttttc   1620
tatttacatg cacaaaaagt accagaaggt gaaaccaata taagtttaac ttcttcaatt   1680
gatacagcat tattgaagaa atccaaagta tatacatttt tttcttcaga gtttatcgat   1740
actatcaata aacctgtaaa tgcagcacta tttatagatt ggataagcaa agtaataaga   1800
gatttaccca ctgaagctac acaaaaaagt actgttgata agattgcaga catatcttta   1860
attgtaccct atgtaggtct tgctttgaat atagttattg aggcagaaaa aggaaatttt   1920
gaggaggcat ttgaattatt aggagcgggt attttattag aatttgtgcc agagcttaca   1980
attcctgtaa ttttagtgtt tacgataaaa tcctatatag attcatatga gaataaaaat   2040
aaagcaatta aagcaataaa taattcatta atcgaaagag aagcaaagtg gaaagaaata   2100
tatagttgga tagtatcaaa ttggcttact agaattaata cgcaatttaa taaaagaaaa   2160
gagcaaatgt atcaggcttt acaaaatcaa gtagatgcaa taaaaacagc aatagaatat   2220
aaatataata attatacttc agatgagaaa aatagacttg aatctaaata taatatcaat   2280
aatatagaag aagaattgaa taaaaaagtt tctttagcaa tgaaaaatat agaaagattt   2340
atgacagaaa gttctatatc ttatttaatg aaattaataa atgaagccga agttggtaaa   2400
ttaaaagaat atgataaaca tgttaagagc gatttattag actatattct ctaccataaa   2460
ttaatcttag gagagcagac aaaggaatta attgatttgg tgactagtac tttgaatagt   2520
agtattccat ttgaactttc ttcatatact aatgataaaa ttctaattat atattttaat   2580
agattatata aaaaaattaa agatagttct attttagata tgcgatatga aaataataaa   2640
tttatagata tctctggata tggttcaaat ataagcatta atggaaacgt atatatttat   2700
tcaacaaata gaaatcaatt tggaatatat agtggtaggc ttagtgaagt taatatagct   2760
caaaataatg atattatata caatagtaga tatcaaaatt ttagtattag tttctgggta   2820
accattccta aacactacag acctatgaat cgtaatcggg aatacactat aataaattgt   2880
atggggaata ataattcggg atggaaaata tcacttagaa ctattagaga ttgtgaaata   2940
atttggactt tacaagatac ttccggaaat aaggaaaaat taattttttag gtatgaagaa   3000 cttgctagta tatctgatta tataaataaa tggattttttg taactattac taataataga   3060
ttaggcaatt ctagaatttta catcaatgga aatttaatag ttgaaaaatc aatttcgaat   3120
ttaggtgata ttcatgttag tgataatata ttatttaaaa ttgttggttg tgatgatgaa   3180
acgtatgttg gtataagata tttttaaagtt tttaatacgg aattagataa aacagaaatt   3240
```

```
gagactttat atagtaatga gccagatcca agtatcttaa aagactattg gggaaattat    3300
ttgctatata ataaaaaata ttatttattc aatttactaa gaaaagataa gtatattact    3360
cggaattcag gcattttaaa tattaatcaa caaagaggtg ttactggagg catatctgtt    3420
tttttgaact ataaattata tgaaggagta gaagttatta taagaaaaaa tgctcctata    3480
gatatatcta atacagataa ttttgttaga aaaaacgatc tagcatacat taatgtagta    3540
gatcatggtg tagaatatcg gttatatgct gatatatcaa ttacaaaatc agagaaaata    3600
ataaaattaa taagaacatc taatccaaac gatagcttag gtcaaattat agttatggat    3660
tcaataggaa ataattgcac aatgaatttt caaaacaatg atgggagcaa tataggatta    3720
ctaggttttc attcagatga tttggttgct agtagttggt attataacca tatacgaaga    3780
aacactagca gtaatggatg cttttggagt tttatttcta aagagcatgg ttggaaagaa    3840
taa                                                                 3843

<210> SEQ ID NO 12
<211> LENGTH: 1280
<212> TYPE: PRT
<213> ORGANISM: Clostridium botulinum

<400> SEQUENCE: 12

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Arg Ser Arg Lys
            20                  25                  30

Tyr Tyr Lys Ala Phe Glu Ile Met Pro Asn Val Trp Ile Met Pro Glu
        35                  40                  45

Arg Asp Thr Ile Gly Thr Lys Pro Asp Glu Phe Gln Val Pro Asp Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Asp Thr Leu Ile Asn Glu Phe
        115                 120                 125

Leu Pro Val Asn Val Thr Thr Ser Val Asn Ile Lys Phe Ser Thr Asp
    130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
    210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
```

```
                260               265               270
Glu Asp Leu Asn Ile Ile Pro Ser Ala Met Lys Glu Lys Ile Tyr Asn
                275               280               285

Asp Leu Leu Ala Asn Tyr Glu Lys Ile Ala Thr Arg Leu Arg Glu Val
            290               295               300

Asn Thr Ala Pro Pro Gly Tyr Asp Ile Asn Glu Tyr Lys Asp Tyr Phe
305               310               315               320

Gln Trp Lys Tyr Gly Leu Asp Arg Asn Ala Asp Gly Ser Tyr Thr Val
                325               330               335

Asn Arg Asn Lys Phe Asn Glu Ile Tyr Lys Lys Leu Tyr Ser Phe Thr
            340               345               350

Glu Ile Asp Leu Ala Asn Lys Phe Lys Val Lys Cys Arg Asn Thr Tyr
                355               360               365

Phe Ile Lys Tyr Gly Phe Val Lys Val Pro Asn Leu Leu Asp Asp Asp
        370               375               380

Ile Tyr Thr Val Ser Glu Gly Phe Asn Ile Gly Asn Leu Ala Val Asn
385               390               395               400

Asn Arg Gly Gln Asn Ile Asn Leu Asn Pro Lys Ile Ile Asp Ser Ile
                405               410               415

Pro Asp Lys Gly Leu Val Glu Lys Ile Ile Lys Phe Cys Lys Ser Ile
            420               425               430

Ile Pro Arg Lys Gly Thr Lys Gln Ser Pro Ser Leu Cys Ile Arg Val
        435               440               445

Asn Asn Arg Glu Leu Phe Phe Val Ala Ser Glu Ser Ser Tyr Asn Glu
    450               455               460

Ser Asp Ile Asn Thr Pro Lys Glu Ile Asp Asp Thr Thr Asn Leu Asn
465               470               475               480

Asn Asn Tyr Arg Asn Asn Leu Asp Glu Val Ile Leu Asp Tyr Asn Ser
                485               490               495

Glu Thr Ile Pro Gln Ile Ser Asn Arg Thr Leu Asn Thr Leu Val Gln
            500               505               510

Asp Asn Ser Tyr Val Pro Arg Tyr Asp Ser Asn Gly Thr Ser Glu Ile
        515               520               525

Glu Glu Tyr Asp Val Val Asp Phe Asn Val Phe Phe Tyr Leu His Ala
    530               535               540

Gln Lys Val Pro Glu Gly Glu Thr Asn Ile Ser Leu Thr Ser Ser Ile
545               550               555               560

Asp Thr Ala Leu Leu Glu Glu Ser Lys Val Tyr Thr Phe Phe Ser Ser
                565               570               575

Glu Phe Ile Asp Thr Ile Asn Lys Pro Val Asn Ala Ala Leu Phe Ile
            580               585               590

Asp Trp Ile Ser Lys Val Ile Arg Asp Phe Thr Thr Glu Ala Thr Gln
        595               600               605

Lys Ser Thr Val Asp Lys Ile Ala Asp Ile Ser Leu Ile Val Pro Tyr
    610               615               620

Val Gly Leu Ala Leu Asn Ile Val Ile Glu Ala Lys Gly Asn Phe
625               630               635               640

Glu Glu Ala Phe Glu Leu Leu Gly Ala Gly Ile Leu Leu Glu Phe Val
                645               650               655

Pro Glu Leu Thr Ile Pro Val Ile Leu Val Phe Thr Ile Lys Ser Tyr
            660               665               670

Ile Asp Ser Tyr Glu Asn Lys Asn Lys Ala Ile Lys Ala Ile Asn Asn
        675               680               685
```

```
Ser Leu Ile Glu Arg Glu Ala Lys Trp Lys Glu Ile Tyr Ser Trp Ile
690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Ala Ile Glu Tyr Lys Tyr Asn Asn Tyr Thr Ser Asp Glu Lys Asn Arg
                740                 745                 750

Leu Glu Ser Lys Tyr Asn Ile Asn Asn Ile Glu Glu Glu Leu Asn Lys
                755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800

Leu Lys Glu Tyr Asp Lys His Val Lys Ser Asp Leu Leu Asp Tyr Ile
                805                 810                 815

Leu Tyr His Lys Leu Ile Leu Gly Glu Gln Thr Lys Glu Leu Ile Asp
                820                 825                 830

Leu Val Thr Ser Thr Leu Asn Ser Ser Ile Pro Phe Glu Leu Ser Ser
                835                 840                 845

Tyr Thr Asn Asp Lys Ile Leu Ile Ile Tyr Phe Asn Arg Leu Tyr Lys
850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Ser Gly
                900                 905                 910

Arg Leu Ser Glu Val Asn Ile Ala Gln Asn Asn Asp Ile Ile Tyr Asn
                915                 920                 925

Ser Arg Tyr Gln Asn Phe Ser Ile Ser Phe Trp Val Thr Ile Pro Lys
                930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
                980                 985                 990

Lys Leu Ile Phe Arg Tyr Glu Glu Leu Ala Ser Ile Ser Asp Tyr Ile
                995                 1000                1005

Asn Lys Trp Ile Phe Val Thr Ile Thr Asn Asn Arg Leu Gly Asn
                1010                1015                1020

Ser Arg Ile Tyr Ile Asn Gly Asn Leu Ile Val Glu Lys Ser Ile
                1025                1030                1035

Ser Asn Leu Gly Asp Ile His Val Ser Asp Asn Ile Leu Phe Lys
                1040                1045                1050

Ile Val Gly Cys Asp Asp Glu Thr Tyr Val Gly Ile Arg Tyr Phe
                1055                1060                1065

Lys Val Phe Asn Thr Glu Leu Asp Lys Thr Glu Ile Glu Thr Leu
                1070                1075                1080

Tyr Ser Asn Glu Pro Asp Pro Ser Ile Leu Lys Asp Tyr Trp Gly
                1085                1090                1095
```

| | | | | | | | | | | |
|---|---|---|---|---|---|---|---|---|---|---|
|Asn|Tyr|Leu|Leu|Tyr|Asn|Lys|Lys|Tyr|Leu|Phe|Asn|Leu|Leu|
| |1100| | | |1105| | | |1110| | | | |
|Arg|Lys|Asp|Lys|Tyr|Ile|Thr|Arg|Asn|Ser|Gly|Ile|Leu|Asn|Ile|
| |1115| | | |1120| | | |1125| | | | | |
|Asn|Gln|Gln|Arg|Gly|Val|Thr|Gly|Gly|Ile|Ser|Val|Phe|Leu|Asn|
| |1130| | | |1135| | | |1140| | | | | |
|Tyr|Lys|Leu|Tyr|Glu|Gly|Val|Glu|Val|Ile|Ile|Arg|Lys|Asn|Ala|
| |1145| | | |1150| | | |1155| | | | | |
|Pro|Ile|Asp|Ile|Ser|Asn|Thr|Asp|Asn|Phe|Val|Arg|Lys|Asn|Asp|
| |1160| | | |1165| | | |1170| | | | | |
|Leu|Ala|Tyr|Ile|Asn|Val|Val|Asp|His|Gly|Val|Glu|Tyr|Arg|Leu|
| |1175| | | |1180| | | |1185| | | | | |
|Tyr|Ala|Asp|Ile|Ser|Ile|Thr|Lys|Ser|Glu|Lys|Ile|Ile|Lys|Leu|
| |1190| | | |1195| | | |1200| | | | | |
|Ile|Arg|Thr|Ser|Asn|Pro|Asn|Asp|Ser|Leu|Gly|Gln|Ile|Ile|Val|
| |1205| | | |1210| | | |1215| | | | | |
|Met|Asp|Ser|Ile|Gly|Asn|Asn|Cys|Thr|Met|Asn|Phe|Gln|Asn|Asn|
| |1220| | | |1225| | | |1230| | | | | |
|Asp|Gly|Ser|Asn|Ile|Gly|Leu|Leu|Gly|Phe|His|Ser|Asp|Asp|Leu|
| |1235| | | |1240| | | |1245| | | | | |
|Val|Ala|Ser|Ser|Trp|Tyr|Tyr|Asn|His|Ile|Arg|Arg|Asn|Thr|Ser|
| |1250| | | |1255| | | |1260| | | | | |
|Ser|Asn|Gly|Cys|Phe|Trp|Ser|Phe|Ile|Ser|Lys|Glu|His|Gly|Trp|
| |1265| | | |1270| | | |1275| | | | | |
|Lys|Glu|
| |1280|

<210> SEQ ID NO 13
<211> LENGTH: 3894
<212> TYPE: DNA
<213> ORGANISM: Clostridium botulinum
<220> FEATURE:
<221> NAME/KEY: misc_feature
<222> LOCATION: (20)..(20)
<223> OTHER INFORMATION: n is a, c, g, or t

<400> SEQUENCE: 13

```
atgccagtta atataaaaan ctttaattat aatgacccta ttaataatga tgacattatt     60
atgatggaac cattcaatga cccagggcca ggaacatatt ataaagcttt taggattata    120
gatcgtattt ggatagtacc agaaaggttt acttatggat tcaacctga ccaatttaat     180
gccagtacag gagtttttag taaagatgtc tacgaatatt acgatccaac ttatttaaaa    240
accgatgctg aaaaagataa attttttaaaa acaatgatta aattatttaa tagaattaat    300
tcaaaaccat caggacagag attactggat atgatagtag atgctatacc ttatcttgga    360
aatgcatcta caccgcccga caaatttgca gcaaatgttg caaatgtatc tattaataaa    420
aaaattatcc aacctggagc tgaagatcaa ataaaaggtt aatgacaaa tttaataata    480
tttggaccag gaccagttct aagtgataat tttactgata gtatgattat gaatggccat    540
tccccaatat cagaaggatt tggtgcaaga atgatgataa gattttgtcc tagttgttta    600
aatgtattta ataatgttca ggaaataaaa gatacatcta tatttagtag acgcgcgtat    660
tttgcagatc cagctctaac gttaatgcat gaacttatac atgtgttaca tggattatat    720
ggaattaaga taagtaattt accaattact ccaaatacaa aagaattttt catgcaacat    780
agcgatcctg tacaagcaga agaactatat acattcggag gacatgatcc tagtgttata    840
```

```
agtccttcta cggatatgaa tatttataat aaagcgttac aaaattttca agatatagct    900
aataggctta atattgtttc aagtgcccaa gggagtggaa ttgatatttc cttatataaa    960
caaatatata aaaataaata tgattttgtt gaagatccta atggaaaata tagtgtagat   1020
aaggataagt ttgataaatt atataaggcc ttaatgtttg gctttactga aactaatcta   1080
gctggtgaat atggaataaa aactaggtat tcttatttta gtgaatattt gccaccgata   1140
aaaactgaaa aattgttaga caatacaatt tatactcaaa atgaaggctt taacatagct   1200
agtaaaaatc tcaaaacgga atttaatggt cagaataagg cggtaaataa agaggcttat   1260
gaagaaatca gcctagaaca tctcgttata tatagaatag caatgtgcaa gcctgtaatg   1320
tacaaaaata ccggtaaatc tgaacagtgt attattgtta ataatgagga tttatttttc   1380
atagctaata aagatagttt ttcaaaagat ttagctaaag cagaaactat agcatataat   1440
acacaaaata atactataga aaataatttt tctatagatc agttgatttt agataatgat   1500
ttaagcagtg gcatagactt accaaatgaa acacagaac catttacaaa ttttgacgac    1560
atagatatcc ctgtgtatat aaacaatct gctttaaaaa aaatttttgt ggatggagat    1620
agccttttg aatatttaca tgctcaaaca tttccttcta atatagaaaa tctacaacta    1680
acgaattcat taaatgatgc tttaagaaat aataataaag tctatacttt tttttctaca   1740
aaccttgttg aaaaagctaa tacagttgta ggtgcttcac tttttgtaaa ctgggtaaaa   1800
ggagtaaatag atgattttac atctgaatcc acacaaaaaa gtactataga taaagttttca  1860
gatgtatcca taattattcc ctatatagga cctgctttga atgtaggaaa tgaaacagct   1920
aaagaaaatt ttaaaatgc ttttgaaata ggtggagccg ctatcttaat ggagtttatt    1980
ccagaactta ttgtacctat agttggattt tttacattag aatcatatgt aggaaataaa   2040
gggcatatta ttatgacgat atccaatgct ttaagaaaaa gggatcaaaa atggacagat   2100
atgtatggtt tgatagtatc gcagtggctc tcaacggtta atactcaatt ttatacaata   2160
aaagaaagaa tgtacaatgc tttaaaataat caatcacaag caatagaaaa aataatagaa   2220
gatcaatata atagatatag tgaagaagat aaaatgaata ttaacattga ttttaatgat   2280
atagatttta aacttaatca aagtataaat ttagcaataa acaatataga tgatttata    2340
aaccaatgtt ctatatcata tctaatgaat agaatgattc cattagctgt aaaaaagtta   2400
aaagactttg atgataatct taagagagat ttattggagt atatagatac aaatgaacta   2460
tatttacttg atgaagtaaa tattctaaaa tcaaagtaa atagacacct aaaagacagt    2520
ataccatttg atctttcact atataccaag gacacaattt taatacaagt ttttaataat   2580
tatattagta atattagtag taatgctatt ttaagtttaa gttatagagg tgggcgttta   2640
atagattcat ctggatatgg tgcaactatg aatgtaggtt cagatgttat ctttaatgat   2700
ataggaaatg gtcaatttaa attaaataat tctgaaaata gtaatattac ggcacatcaa   2760
agtaaattcg ttgtatatga tagtatgtttt gataatttta gcattaactt ttgggtaagg   2820
actcctaaat ataataataa tgatatacaa acttatcttc aaaatgagta tacaataatt   2880
agttgtataa aaatgactc aggatggaaa gtatctatta agggaaatag aataatatgg    2940
acattaatag atgttaatgc aaaatctaaa tcaatatttt tcgaatatag tataaaagat   3000
aatatatcag attatataaa taaatggttt tccataacta ttactaatga tagattaggt   3060
aacgcaaata tttatataaa tggaagtttg aaaaaaagtg aaaaaatttt aaacttagat   3120
agaattaatt ctagtaatga tatagacttc aaattaatta attgtacaga tactactaaa   3180
tttgtttgga ttaaggattt taatattttt ggtagagaat aaaatgctac agaagtatct   3240
```

```
tcactatatt ggattcaatc atctacaaat actttaaaag attttggggg gaatcctttta    3300 agatacgata cacaatacta tctgtttaat caaggtatgc aaaatatcta tataaagtat    3360
tttagtaaag cttctatggg ggaaactgca ccacgtacaa actttaataa tgcagcaata    3420
aattatcaaa atttatatct tggtttacga tttattataa aaaaagcatc aaattctcgg    3480
aatataaata atgataatat agtcagagaa ggagattata tatatcttaa tattgataat    3540
atttctgatg aatcttacag agtatatgtt ttggtgaatt ctaaagaaat tcaaactcaa    3600 ttattttttag cacccataaa tgatgatcct acgttctatg atgtactaca aataaaaaaa    3660
tattatgaaa aaacaacata taattgtcag atactttgcg aaaaagatac taaaacattt    3720
gggctgtttg gaattggtaa atttgttaaa gattatggat atgtttggga tacctatgat    3780
aattattttt gcataagtca gtggtatctc agaagaatat ctgaaaatat aaataaatta    3840
aggttgggat gtaattggca attcattccc gtggatgaag gatggacaga ataa          3894
```

<210> SEQ ID NO 14
<211> LENGTH: 1297
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 14

```
Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240
```

```
Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655
```

```
Met Glu Phe Ile Pro Glu Leu Ile Val Pro Ile Val Gly Phe Phe Thr
              660                 665                 670

Leu Glu Ser Tyr Val Gly Asn Lys Gly His Ile Ile Met Thr Ile Ser
          675                 680                 685

Asn Ala Leu Lys Lys Arg Asp Gln Lys Trp Thr Asp Met Tyr Gly Leu
      690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
        995                 1000                1005

Trp Phe Ser Ile Thr Ile Thr Asn Asp Arg Leu Gly Asn Ala Asn
    1010                1015                1020

Ile Tyr Ile Asn Gly Ser Leu Lys Lys Ser Glu Lys Ile Leu Asn
    1025                1030                1035

Leu Asp Arg Ile Asn Ser Ser Asn Asp Ile Asp Phe Lys Leu Ile
    1040                1045                1050

Asn Cys Thr Asp Thr Thr Lys Phe Val Trp Ile Lys Asp Phe Asn
    1055                1060                1065

Ile Phe Gly Arg Glu Leu Asn Ala Thr Glu Val Ser Ser Leu Tyr
```

Trp Ile Gln Ser Ser Thr Asn Thr Leu Lys Asp Phe Trp Gly Asn
         1070               1075                1080

Pro Leu Arg Tyr Asp Thr Gln Tyr Tyr Leu Phe Asn Gln Gly Met
     1085               1090                1095

Gln Asn Ile Tyr Ile Lys Tyr Phe Ser Lys Ala Ser Met Gly Glu
 1100               1105                1110

Thr Ala Pro Arg Thr Asn Phe Asn Asn Ala Ala Ile Asn Tyr Gln
         1115               1120                1125

Asn Leu Tyr Leu Gly Leu Arg Phe Ile Ile Lys Lys Ala Ser Asn
     1130               1135                1140

Ser Arg Asn Ile Asn Asn Asp Asn Ile Val Arg Glu Gly Asp Tyr
 1145               1150                1155

Ile Tyr Leu Asn Ile Asp Asn Ile Ser Asp Glu Ser Tyr Arg Val
         1160               1165                1170

Tyr Val Leu Val Asn Ser Lys Glu Ile Gln Thr Gln Leu Phe Leu
     1175               1180                1185

Ala Pro Ile Asn Asp Asp Pro Thr Phe Tyr Asp Val Leu Gln Ile
 1190               1195                1200

Lys Lys Tyr Tyr Glu Lys Thr Thr Tyr Asn Cys Gln Ile Leu Cys
         1205               1210                1215

Glu Lys Asp Thr Lys Thr Phe Gly Leu Phe Gly Ile Gly Lys Phe
     1220               1225                1230

Val Lys Asp Tyr Gly Tyr Val Trp Asp Thr Tyr Asp Asn Tyr Phe
 1235               1240                1245

Cys Ile Ser Gln Trp Tyr Leu Arg Arg Ile Ser Glu Asn Ile Asn
         1250               1255                1260

Lys Leu Arg Leu Gly Cys Asn Trp Gln Phe Ile Pro Val Asp Glu
     1265               1270                1275

Gly Trp Thr Glu
 1280

<210> SEQ ID NO 15
<211> LENGTH: 4400
<212> TYPE: DNA
<213> ORGANISM: Clostridium tetani

<400> SEQUENCE: 15
tagcattaaa aaaattagaa cctatagtaa ataaattaat taatatatag tttttataat      60
ttaattatga ataatattct taagataaaa agtaaatttt taaaaattta aattttcagt     120
ttacaaaaaa taacctgatt atgttatatg taattgtaaa aaacatataa aaaatcagaa     180
aaatttagga ggtatattat taatggatta ataataatt ttttaattta cttttgatta     240
ataaatatta aatgtttatt ttaattagga gatgatacgt atgccaataa ccataaataa     300
ttttagatat agtgatcctg ttaataatga tacaattatt atgatggagc caccatactg     360
taagggtcta gatatctatt ataaggcttt caaaataaca gatcgtattt ggatagtgcc     420
ggaaaggtat gaatttggga caaaacctga gatttttaac ccaccatctt cattaataga     480
aggtgcatct gagtattacg atccaaatta tttaaggact gattctgata agatagatt      540
tttacaaacc atggtaaaac tgtttaacag aattaaaaac aatgtagcag gtgaagcctt     600
attagataag ataataaatg ccatacctta ccttggaaat tcatattcct tactagacaa     660
gtttgataca aactctaatt cagtatcttt taatttatta gaacaagacc ccagtggagc     720

```
aactacaaaa tcagcaatgc tgacaaattt aataatattt ggacctgggc ctgttttaaa    780
taaaaatgag gttagaggta ttgtattgag ggtagataat aaaaattact tcccatgtag    840
agatggtttt ggctcaataa tgcaaatggc attttgccca gaatatgtac ctacctttga    900
taatgtaata gaaaatatta cgtcactcac tattggcaaa agcaaatatt ttcaagatcc    960
agcattacta ttaatgcacg aacttataca tgtactacat ggtttatacg gaatgcaggt   1020
atcaagccat gaaattattc catccaaaca gaaatttat atgcagcata catatccaat    1080
aagtgctgaa gaactattca cttttggcgg acaggatgct aatcttataa gtattgatat   1140
aaaaaacgat ttatatgaaa aaactttaaa tgattataaa gctatagcta acaaacttag   1200
tcaagtcact agctgcaatg atcccaacat tgatattgat agctacaaac aaatatatca   1260
acaaaaatat caattcgata agatagcaa tggacaatat attgtaaatg aggataaatt    1320
tcagatacta taatagca taatgtatgg ttttacagag attgaattgg gaaaaaaatt     1380
taatataaaa actagacttt cttattttag tatgaatcat gaccctgtaa aaattccaaa   1440
tttattagat gatacaattt acaatgatac agaaggattt aatatagaaa gcaaagatct   1500
gaaatctgaa tataaaggac aaaatatgag ggtaaataca aatgctttta gaaatgttga   1560
tggatcaggc ctagtttcaa aacttattgg cttatgtaaa aaaattatac caccaacaaa   1620
tataagagaa aatttatata atagaactgc atcattaaca gatttaggag gagaattatg   1680
tataaaaatt aaaaatgaag atttaacttt tatagctgaa aaaaatagct ttcagaaga    1740 accatttcaa gatgaaatag ttagttataa tacaaaaaat aaaccattaa attttaatta   1800
ttcgctagat aaaattattg tagattataa tctacaaagt aaaattacat tacctaatga   1860
taggacaacc ccagttacaa aaggaattcc atatgctcca gaatataaaa gtaatgctgc   1920
aagtacaata gaaatacata atattgatga caatacaata tatcaatatt tgtatgctca   1980
aaaatctcct acaactctac aaagaataac tatgactaat tctgttgatg acgcattaat   2040
aaattccacc aaaatatatt catattttcc atctgtaatc agtaaagtta accaaggtgc   2100
acaaggaatt ttattcttac agtgggtgag agatataatt gatgattta ccaatgaatc    2160 ttcacaaaaa actactattg ataaaatttc agatgtatcc actattgttc cttatatagg   2220
acccgcatta acattgtaa acaaggcta tgagggaaac tttataggcg ctttagaaac    2280
taccggagtg gttttattat tagaatatat tccagaaatt actttaccag taattgcagc   2340
tttatctata gcagaaagta gcacacaaaa agaaaagata ataaaaacaa tagataactt   2400
tttagaaaaa agatatgaaa aatggattga agtatataaa ctagtaaaag caaaatggtt   2460
aggcacagtt aatacgcaat tccaaaaaag aagttatcaa atgtatagat ctttagaata   2520
tcaagtagat gcaataaaaa aataataga ctatgaatat aaaatatatt caggacctga    2580
taaggaacaa attgccgacg aaattaataa tctgaaaaac aaacttgaag aaaaggctaa   2640
taaagcaatg ataaacataa atatatttat gagggaaagt tctagatcat ttttagttaa   2700
tcaaatgatt aacgaagcta aaaagcagtt attagagttt gatactcaaa gcaaaaatat   2760
tttaatgcag tatataaaag caaattctaa atttataggt ataactgaac taaaaaaatt   2820
agaatcaaaa ataaacaaag ttttttcaac accaattcca ttttcttatt ctaaaaatct   2880
ggattgttgg gttgataatg aagaagatat agatgttata ttaaaaaaga gtacaatttt   2940
aaatttagat attaataatg atattatatc agatatatct gggtttaatt catctgtaat   3000
aacatatcca gatgctcaat tggtgcccgg aataaatggc aaagcaatac atttagtaaa   3060
caatgaatct tctgaagtta tagtgcataa agctatggat attgaatata atgatatgtt   3120
```

```
taataatttt accgttagct tttggttgag ggttcctaaa gtatctgcta gtcatttaga      3180
acaatatggc acaaatgagt attcaataat tagctctatg aaaaaacata gtctatcaat      3240
aggatctggt tggagtgtat cacttaaagg taataactta atatggactt taaaagattc      3300
cgcgggagaa gttagacaaa taacttttag ggatttacct gataaattta atgcttattt      3360
agcaaataaa tgggttttta taactattac taatgataga ttatcttctg ctaatttgta      3420
tataaatgga gtacttatgg gaagtgcaga aattactggt ttaggagcta ttagagagga      3480
taataatata acattaaaac tagatagatg taataataat aatcaatacg tttctattga      3540
taaatttagg atattttgca aagcattaaa tccaaaagag attgaaaaat tatacacaag      3600
ttatttatct ataaccttt taagagactt ctggggaaac cctttacgat atgatacaga      3660
atattattta ataccagtag cttctagttc taaagatgtt caattgaaaa atataacaga      3720
ttatatgtat ttgacaaatg cgccatcgta tactaacgga aaattgaata tatattatag      3780
aaggttatat aatggactaa aatttattat aaaaagatat acacctaata atgaaataga      3840
ttcttttgtt aaatcaggtg atttttattaa attatatgta tcatataaca ataatgagca      3900
cattgtaggt tatccgaaag atggaaatgc ctttaataat cttgatagaa ttctaagagt      3960
aggttataat gccccaggta tccctctta taaaaaaatg gaagcagtaa aattgcgtga      4020
tttaaaaacc tattctgtac aacttaaatt atatgatgat aaaaatgcat ctttaggact      4080
agtaggtacc cataatggtc aaataggcaa cgatccaaat agggatatat taattgcaag      4140
caactggtac tttaatcatt taaaagataa aattttagga tgtgattggt actttgtacc      4200
tacagatgaa ggatggacaa atgattaaac agattgatat gttcatgatt actctatata      4260
aaaaattaaa taatataaca atctagctat attatttttg attattttct taatatatac      4320
taataaaata atcaaaatag agcctatctt aaattactga agggctgtgt caaaataaga      4380
ttttgacaca gcctctactt                                                 4400
```

<210> SEQ ID NO 16
<211> LENGTH: 1315
<212> TYPE: PRT
<213> ORGANISM: Clostridium tetani

<400> SEQUENCE: 16

```
Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
        50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
        130                 135                 140
```

-continued

```
Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
            165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
            195                 200                 205

Val Ile Glu Asn Ile Thr Ser Leu Thr Ile Gly Lys Ser Lys Tyr Phe
            210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
            245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
            325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
            370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
            405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
            485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
530                 535                 540

Asn Ala Ala Ser Thr Ile Glu Ile His Asn Ile Asp Asp Asn Thr Ile
545                 550                 555                 560
```

Tyr Gln Tyr Leu Tyr Ala Gln Lys Ser Pro Thr Thr Leu Gln Arg Ile
            565                 570                 575
Thr Met Thr Asn Ser Val Asp Asp Ala Leu Ile Asn Ser Thr Lys Ile
        580                 585                 590
Tyr Ser Tyr Phe Pro Ser Val Ile Ser Lys Val Asn Gln Gly Ala Gln
        595                 600                 605
Gly Ile Leu Phe Leu Gln Trp Val Arg Asp Ile Asp Asp Phe Thr
        610                 615                 620
Asn Glu Ser Ser Gln Lys Thr Thr Ile Asp Lys Ile Ser Asp Val Ser
625                 630                 635                 640
Thr Ile Val Pro Tyr Ile Gly Pro Ala Leu Asn Ile Val Lys Gln Gly
            645                 650                 655
Tyr Glu Gly Asn Phe Ile Gly Ala Leu Glu Thr Thr Gly Val Val Leu
            660                 665                 670
Leu Leu Glu Tyr Ile Pro Glu Ile Thr Leu Pro Val Ile Ala Ala Leu
        675                 680                 685
Ser Ile Ala Glu Ser Ser Thr Gln Lys Glu Lys Ile Ile Lys Thr Ile
        690                 695                 700
Asp Asn Phe Leu Glu Lys Arg Tyr Glu Lys Trp Ile Glu Val Tyr Lys
705                 710                 715                 720
Leu Val Lys Ala Lys Trp Leu Gly Thr Val Asn Thr Gln Phe Gln Lys
            725                 730                 735
Arg Ser Tyr Gln Met Tyr Arg Ser Leu Glu Tyr Gln Val Asp Ala Ile
            740                 745                 750
Lys Lys Ile Ile Asp Tyr Glu Tyr Lys Ile Tyr Ser Gly Pro Asp Lys
            755                 760                 765
Glu Gln Ile Ala Asp Glu Ile Asn Asn Leu Lys Asn Lys Leu Glu Glu
        770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
            805                 810                 815
Leu Leu Glu Phe Asp Thr Gln Ser Lys Asn Ile Leu Met Gln Tyr Ile
            820                 825                 830
Lys Ala Asn Ser Lys Phe Ile Gly Ile Thr Glu Leu Lys Lys Leu Glu
        835                 840                 845
Ser Lys Ile Asn Lys Val Phe Ser Thr Pro Ile Pro Phe Ser Tyr Ser
    850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
            885                 890                 895
Ser Asp Ile Ser Gly Phe Asn Ser Ser Val Ile Thr Tyr Pro Asp Ala
            900                 905                 910
Gln Leu Val Pro Gly Ile Asn Gly Lys Ala Ile His Leu Val Asn Asn
            915                 920                 925
Glu Ser Ser Glu Val Ile Val His Lys Ala Met Asp Ile Glu Tyr Asn
    930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
            965                 970                 975
Ile Ser Ser Met Lys Lys His Ser Leu Ser Ile Gly Ser Gly Trp Ser

-continued

```
                980             985             990
Val Ser Leu Lys Gly Asn Asn Leu Ile Trp Thr Leu Lys Asp Ser Ala
        995                 1000                1005
Gly Glu Val Arg Gln Ile Thr Phe Arg Asp Leu Pro Asp Lys Phe
    1010                1015                1020
Asn Ala Tyr Leu Ala Asn Lys Trp Val Phe Ile Thr Ile Thr Asn
    1025                1030                1035
Asp Arg Leu Ser Ser Ala Asn Leu Tyr Ile Asn Gly Val Leu Met
    1040                1045                1050
Gly Ser Ala Glu Ile Thr Gly Leu Gly Ala Ile Arg Glu Asp Asn
    1055                1060                1065
Asn Ile Thr Leu Lys Leu Asp Arg Cys Asn Asn Asn Gln Tyr
    1070                1075                1080
Val Ser Ile Asp Lys Phe Arg Ile Phe Cys Lys Ala Leu Asn Pro
    1085                1090                1095
Lys Glu Ile Glu Lys Leu Tyr Thr Ser Tyr Leu Ser Ile Thr Phe
    1100                1105                1110
Leu Arg Asp Phe Trp Gly Asn Pro Leu Arg Tyr Asp Thr Glu Tyr
    1115                1120                1125
Tyr Leu Ile Pro Val Ala Ser Ser Ser Lys Asp Val Gln Leu Lys
    1130                1135                1140
Asn Ile Thr Asp Tyr Met Tyr Leu Thr Asn Ala Pro Ser Tyr Thr
    1145                1150                1155
Asn Gly Lys Leu Asn Ile Tyr Tyr Arg Arg Leu Tyr Asn Gly Leu
    1160                1165                1170
Lys Phe Ile Ile Lys Arg Tyr Thr Pro Asn Asn Glu Ile Asp Ser
    1175                1180                1185
Phe Val Lys Ser Gly Asp Phe Ile Lys Leu Tyr Val Ser Tyr Asn
    1190                1195                1200
Asn Asn Glu His Ile Val Gly Tyr Pro Lys Asp Gly Asn Ala Phe
    1205                1210                1215
Asn Asn Leu Asp Arg Ile Leu Arg Val Gly Tyr Asn Ala Pro Gly
    1220                1225                1230
Ile Pro Leu Tyr Lys Lys Met Glu Ala Val Lys Leu Arg Asp Leu
    1235                1240                1245
Lys Thr Tyr Ser Val Gln Leu Lys Leu Tyr Asp Asp Lys Asn Ala
    1250                1255                1260
Ser Leu Gly Leu Val Gly Thr His Asn Gly Gln Ile Gly Asn Asp
    1265                1270                1275
Pro Asn Arg Asp Ile Leu Ile Ala Ser Asn Trp Tyr Phe Asn His
    1280                1285                1290
Leu Lys Asp Lys Ile Leu Gly Cys Asp Trp Tyr Phe Val Pro Thr
    1295                1300                1305
Asp Glu Gly Trp Thr Asn Asp
    1310                1315
```

METHODS FOR ENHANCING THE SPECIFIC UPTAKE OF BOTULINUM NEUROTOXINS INTO CELLS

The present invention provides a method for enhancing the specific uptake of a neurotoxin polypeptide into cells, the method comprising: incubating cells susceptible to neurotoxin intoxication with a neurotoxin polypeptide for a time and under conditions which allow for the neurotoxin polypeptide to exert its biological activity, the incubation comprising at least one of the following steps: (i) $K^+$-mediated depolarization of the cells, (ii) a reduced neurotoxin polypeptide exposition time and/or (iii) agitation of the cells during neurotoxin polypeptide exposition, thereby enhancing the specific uptake of the neurotoxin polypeptide into said cells. In addition, the invention pertains to a method for directly determining the biological activity of a neurotoxin polypeptide in cells, comprising: a) incubating cells susceptible to neurotoxin intoxication with a neurotoxin polypeptide for a time and under conditions which allow for the neurotoxin polypeptide to exert its biological activity, the incubation comprising at least one of the following steps: (i) $K^+$-mediated depolarization of the cells, (ii) a reduced neurotoxin polypeptide exposition time and/or (iii) agitation of the cells during neurotoxin polypeptide exposition; b) fixing the cells and, optionally, permeabilizing the cells with a detergent; c) contacting the cells with at least a first capture antibody specifically binding to the non-cleaved and neurotoxin-cleaved substrate and with at least a second capture antibody specifically binding to the cleavage site of the neurotoxin-cleaved substrate, under conditions which allow for binding of said capture antibodies to said substrates; d) contacting the cells with at least a first detection antibody specifically binding to the first capture antibody, under conditions which allow for binding of said first detection antibody to said first capture antibody, thus forming first detection complexes and with at least a second detection antibody specifically binding to the second capture antibody, under conditions which allow for binding of said second detection antibody to said second capture antibody, thus forming second detection complexes; e) determining the amount of the first and second detection complexes of step d); and f) calculating the amount of substrate cleaved by said neurotoxin polypeptide in said cells by means of the second detection complexes, thereby determining the biological activity of said neurotoxin polypeptide in said cells.

*Clostridium botulinum* and *Clostridium tetani* produce highly potent neurotoxins, i.e. Botulinum toxins (BoNTs) and Tetanus toxin (TeNT), respectively. These Clostridial neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active neurotoxin consists of two chains, an N-terminal light chain of approx. 50 kDa and a heavy chain of approx. 100 kDa linked by a disulfide bond. CNTs structurally and functionally consist of three domains, i.e. the catalytic light chain, the heavy chain encompassing the translocation domain (N-terminal half) and the receptor binding domain (C-terminal half); see, e.g., Krieglstein 1990, Eur. J. Biochem. 188, 39; Krieglstein 1991, Eur. J. Biochem. 202, 41; Krieglstein 1994, J. Protein Chem. 13, 49. The Botulinum neurotoxins are synthesized as molecular complexes comprising the 150 kDa neurotoxin protein and associated non-toxic proteins. The complex sizes differ based on the Clostridial strain and the distinct neurotoxin serotypes ranging from 300 kDa, over 500 kDa, and 900 kDa. The non-toxic proteins in these complexes stabilize the neurotoxin and protect it against degradation; see Silberstein 2004, Pain Practice 4, S19-S26.

*Clostridium botulinum* secretes seven antigenically distinct serotypes designated A to G of the Botulinum neurotoxin (BoNT/A-BoNT/G). All serotypes together with the related Tetanus neurotoxin (TeNT) secreted by *Clostridium tetani*, are Zn2+-endoproteases that block synaptic exocytosis by cleaving SNARE proteins; see Couesnon, 2006, Microbiology, 152, 759. CNTs cause the flaccid muscular paralysis seen in botulism and tetanus; see Fischer 2007, PNAS 104, 10447. Recently, a new Botulinum toxin type, i.e. BoNT/H, has been identified; see Barash and Arnon, J. Infect. Dis. (2014), 209 (2): 183-191 and Dover, Barash, Hill, Xie and Amon, J. Infect. Dis. (2014), 209(2): 192-202.

Despite its toxic effects, the Botulinum toxin complex has been used as a therapeutic agent in a large number of diseases. Botulinum toxin serotype A was approved for human use in the United States in 1989 for the treatment of strabism, blepharospasm, and other disorders. It is commercially available as Botulinum toxin A (BoNT/A) protein preparation, for example, under the trade name BOTOX (Allergan, Inc.) or under the trade name DYSPORT/RELOXIN (Ipsen, Ltd). An improved, complex-free Botulinum toxin A preparation is commercially available under the trade name XEOMIN (Merz Pharma GmbH & Co. KGaA). For therapeutic applications, the preparation is injected directly into the muscle to be treated. At physiological pH, the toxin is released from the protein complex and the desired pharmacological effect takes place. The effect of Botulinum toxin is only temporary, which is the reason why repeated administration of Botulinum toxin may be required to maintain a therapeutic affect.

The Clostridial neurotoxins weaken voluntary muscle strength and are effective therapy for strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction; see Jost 2007, Drugs 67, 669.

During the manufacturing process of Clostridial neurotoxins, the qualitative and quantitative determination of said neurotoxins as well as the quality control of the biologically active neurotoxin polypeptides is of particular importance. In addition, governmental agencies accept only simple, reliable, and validated Botulinum toxin activity assays. At present the mouse $LD_{50}$ bioassay, a lethality test, remains the "gold standard" used by pharmaceutical manufacturers to analyze the potency of their preparations; see Arnon et al. (2001), JAMA 285, 1059-1070. However, in recent years, considerable effort has been undertaken to seek for alternative approaches to alleviate the need for animal testing and all the disadvantages, costs and ethical concerns associated with this type of animal-based assays. In addition, the regulatory agencies are engaging pharmaceutical companies to apply the three "Rs" principle to the potency testing of Botulinum neurotoxins: "Reduce, Refine, Replace"; see Straughan, Altern. Lab. Anim. (2006), 34, 305-313. As a consequence, cell-based test systems have been developed in order to provide reasonable alternatives to methods using live animals. Yet, only three cellular test systems are available for the determination of neurotoxin biological activity thus far which have been shown to be sufficiently sensitive to neurotoxin polypeptides. These cell-based test systems include the use of primary neurons isolated from rodent embryos which are differentiated in vitro (Pellett et al. (2011), Biochem. Biophys. Res. Commun. 404, 388-392), neuronal differentiated induced pluripotent stem cells (Whitemarsh et al. (2012), Toxicol. Sci. 126, 426-35), and a subclone of the SiMa cell line (WO 2010/105234 A1).

However, the isolation of primary neurons requires the killing of animals and is laborious and time consuming. Further, test systems using different primary neurons show large variances. Similarly, the generation of neuronal differentiated induced pluripotent stem cells is difficult and time consuming. In addition, storage of such cells is very problematic. Assays using tumor cell lines are frequently not sensitive enough to BoNT. Moreover, complex differentiation protocols are required for said tumor cell lines which result in large variances and/or high failure rates of assays using said cell lines.

In light of the above, further test systems for the determination of neurotoxin polypeptide activity are highly desirable.

Thus, the technical problem underlying the present invention may be seen as the provision of means and methods complying with the aforementioned needs. The technical problem is solved by the embodiments characterized in the claims and herein below.

In a first aspect, the present invention pertains to a method for enhancing the specific uptake of a neurotoxin polypeptide into cells, the method comprising: incubating cells susceptible to neurotoxin intoxication with a neurotoxin polypeptide for a time and under conditions which allow for the neurotoxin polypeptide to exert its biological activity, the incubation comprising at least one of the following steps: (i) $K^+$-mediated depolarization of the cells, (ii) a reduced neurotoxin polypeptide exposition time and/or (iii) agitation of the cells during neurotoxin polypeptide exposition, thereby enhancing the specific uptake of the neurotoxin polypeptide into said cells. Preferably, this method is an in vitro method.

Clostridial neurotoxin polypeptides act within the synaptic terminal to block neurotransmitter release. The neurotoxin enters the neuron by binding to neuronal membrane receptors, being taken up into an endosome-like compartment, and penetrating the endosome membrane via a pH-dependent translocation process. Once within the synaptic cytoplasm, the Clostridial neurotoxins cleave their corresponding SNARE protein substrates, required for synaptic vesicle fusion.

More specifically, Clostridial neurotoxins are characterized in that they specifically inhibit the secretion of neurotransmitters from pre-synaptic nerve endings. The selectivity for peripheral neurons is mediated by the recognition of different receptors, such as SV2 and GT1b. For example, the specific uptake of BoNT/A into pre-synaptic nerve terminals is a tightly controlled multistep process, involving a combination of high and low affinity receptors. Binding to the ganglioside GT1b mediates an initial binding step and via this concentrates BoNT/A on the cell surface. Once anchored in the membrane, lateral movements within the plasma membrane facilitate intermolecular interactions of BoNT/A with additional (protein) receptors, such as SV2 or FGFR3. The receptor for BoNT/A is the ganglioside GT1b with a binding pocket within the C-terminal portion of the receptor binding domain. According to the APR receptor model, an array of presynaptic receptors (APRs), clustered in microdomains at the presynaptic membrane, are responsible for specific uptake of neurotoxins, including BoNT/A. It is the binding to ganglioside GT1b that mediates the initial binding step and concentrates BoNT/A on the cell surface. Once anchored in the membrane, lateral movements within the plasma membrane facilitate intermolecular interaction of BoNT/A with protein receptors, including the three isoforms of Synaptic Vesicle (SV) glycoprotein 2, SV2A (ENSG00000159164), B (ENSG00000185518) and C (ENSG00000122012) that are exposed on the outer plasma membrane after fusion of synaptic vesicles to the presynaptic membrane. BoNT/A specifically recognizes the fourth luminal domain (LD4) of SV2. The specific sequence in the BoNT/A binding domain that interacts with SV2 has not yet been identified. Glycosylated SV2A, B, and C have also been identified as receptors for BoNT/F and glycosylated SV2A and B have been identified as receptors for BoNT/E. BoNT/D was reported to enter neurons via two ganglioside binding sites, one site at a position previously identified in BoNT/A, B, E, F, and G, and the other site resembling the second ganglioside-binding pocket of TeNT. Recently, BoNT/D has also been shown to use SV2 (all three iso forms) to enter hippocampal neurons, but BoNT/D bound SV2 via a mechanism distinct from BoNT/A and BoNT/E. SV2A and SV2B have also been reported to mediate binding and entry of TeNT into central neurons; see Jacky et al., PLoS Pathog. 2013 May; 9(5): e1003369 and references cited therein.

The physiological effect of the neurotoxins is based on the cleavage of a protein of the SNARE complex subsequent to the binding of the receptor and the translocation of the neurotoxin's light chain. The determination of the biological activity of Clostridial neurotoxins is an important aspect in the characterization of said neurotoxin proteins and is required, inter alia, by regulatory authorities for the clearance of Clostridial neurotoxin-containing products. A reliable test for the measurement of the biological activity of Clostridial neurotoxins is, therefore, basis for research, development and marketing of products containing Clostridial neurotoxins. Furthermore, cell-based test systems shall replace the thus far predominant animal tests for ethical reasons. For establishing such cell-based test systems, a sufficient high sensitivity of neuronal cells or cell lines towards Clostridial neurotoxins is essential.

It has advantageously been found by the present inventors that the specific uptake of Clostridial neurotoxin polypeptides into cells susceptible to Clostridial neurotoxin intoxication can be increased by at least one of the following steps: (i) $K^+$-mediated depolarization of the cells, (ii) a reduced neurotoxin polypeptide exposition time or (iii) agitation of the cells during neurotoxin polypeptide exposition. At the same time, the unspecific uptake of the neurotoxin polypeptide or degradation products thereof can be reduced, by these measures. In particular, the unspecific cellular uptake of the mentioned neurotoxin or degradation products thereof is decreased, by a reduction of the time period in which the cells are incubated with the neurotoxin. The $K^+$-mediated depolarization of the cells stimulates the specific uptake of the neurotoxin. Further, agitation of the cells upon neurotoxin intoxication influences the biophase concentration adjacent to the neuronal membrane and is thereby able to reduce the unspecific uptake as well as to increase the specific uptake of the neurotoxin, into the cells. The corresponding data is shown in the following examples. Further, FIG. 1 shows a comparison of three cell based assay examples where the stressed samples show a comparable kinetic in decay to the referenced assay, the mouse $LD_{50}$ bioassay.

Accordingly, in one aspect of the method of the invention, the unspecific cellular uptake of the neurotoxin polypeptide or degradation products thereof is reduced.

The present invention also comprises selectivity for impaired molecules, e.g. by degradation as an effect of stability storage of Botulinum neurotoxin. As the release of neurotransmitter is induced by $K^+$-mediated depolarization, the following increase in re-uptake of vesicles comprises specific uptake by binding to receptors like GT1b and/or members of the SV2 protein family. An impaired molecule may exhibit a weaker or no binding to a receptor. The same holds true for physical influences like shaking. A less stable binding of the impaired molecule will even be reduced by shaking.

In order to enhance the specific uptake of a neurotoxin polypeptide into cells which are susceptible to neurotoxin intoxication are incubated with a neurotoxin polypeptide for a time period and under conditions which allow for the neurotoxin polypeptide to exert its biological activity. Such time periods and cell culture conditions are known in the art. In the methods of the invention, the cell culture conditions comprise at least one of the following steps: (i) $K^+$-mediated depolarization of the cells, (ii) a reduced neurotoxin polypeptide exposition time or (iii) agitation of the cells during neurotoxin polypeptide exposition. The method of the invention can also encompass at least two of the mentioned steps, for example, steps (i) and (ii), steps (i) and (iii), steps (ii) and (iii), or all three of the steps (i) to (iii). It is preferred that the cell culture conditions comprise each of the following steps, i.e. (i) $K^+$-mediated depolarization of the cells, (ii) a reduced neurotoxin polypeptide exposition time and (iii) agitation of the cells during neurotoxin polypeptide exposition.

Usually, the cell culture medium used in neurotoxin activity assays in the art contains about 5 mM K. Neurons usually establish an ion gradient by actively transporting $K^+$ ions from the medium into the cell and $Na^+$ ions from the cytosol through the plasma membrane to the outside of the cell. The result is a membrane potential which is strictly regulated by the cell and which is the basis of several different cellular processes including communication between cells. A sudden change of the specific ion permeability of the plasma membrane or rapid alteration of the ionic composition at either side of the membrane leads to a change of the membrane potential called depolarization. The $K^+$-mediated depolarization of the cells can be carried out at an increased $K^+$ concentration in the cell culture medium, for example, an additional $K^+$ concentration of about 10 mM, 20 mM, 30 mM, 40 mM, 50 mM, or 55 mM. The final concentration of $K^+$ in the methods of the invention can be about 15 mM, 25 mM, 30 mM, 35 mM, 40 mM, 45 mM, 50 mM, 55 mM or 60 mM $K^+$. The time period for the $K^+$-mediated depolarization is at least for about 30 minutes, 1 hour, 1 and a half hours, 2 hours, 2 and a half hours, 3 hours or even longer.

The $K^+$-mediated depolarization of the cells and/or the neurotoxin polypeptide exposition can be performed in the presence of the ganglioside GT1b. GT1b can be used in a concentration of about 5, 10, 15, 20, 25, 30, 35, 40, 45, 50, 55, or 60 µM, preferably between about 15 µM and about 50 µM, more preferably about 20 µM.

The neurotoxin polypeptide exposition time used in the art is usually between about 4 hours and about 96 hours, frequently about 72 hours. The reduced neurotoxin polypeptide exposition time is intoxication of the cells with the neurotoxin polypeptide for at least 24 hours and less than 96 hours, preferably for at least 48 hours, at least 60 hours, and 72 hours at maximum.

The agitation of the cells during neurotoxin polypeptide exposition can be carried out by using means and methods known in the art, e.g., a magnetic stirrer, rotating spinner flasks or shaking of the cells by utilizing shakers. Agitation of the cells is performed at an appropriate cell culture medium flow rate which avoids the detachment of the cells from the tissue flask. Suitable mean flow rates of the medium are, for example, between about 25 cm/min and about 300 cm/min.

The aforementioned $K^+$-mediated depolarization of the cells can be also carried out in the presence of GT1b and neurotoxin polypeptide, followed by a neurotoxin polypeptide exposition for an additional time period, such as about 24 hours, 36 hours, 48 hours, 60 hours or 72 hours, under agitation.

It is also envisaged that an incubation time without neurotoxin polypeptide precedes the neurotoxin polypeptide exposition. For instance, the incubation time without neurotoxin polypeptide can be, about 6, 12, 18, 24, 30, 36, 42, 48, 54, or 60 hours, preferably between about 16 and about 48 hours.

Further preferred embodiments of the methods of the invention can be derived from the following examples.

The term "neurotoxin polypeptide" or briefly "neurotoxin" or "toxin" as referred to herein denotes Clostridial neurotoxins, i.e. *Clostridium botulinum* and *Clostridium tetani* neurotoxins, in particular Botulinum neurotoxins (BoNTs) and Tetanus neurotoxin (TeNT). More specifically, said term encompasses BoNT/A, BoNT/B, BoNT/C1, BoNT/D, BoNT/E, BoNT/F, BoNT/G, BoNT/H (Barash and Amon, J. Infect. Dis. (2014), 209 (2): 183-191) and Tetanus neurotoxin (TeNT), as well as subtypes thereof. For example, the subtypes of BoNT/A include BoNT/A1, BoNT/A2, BoNT/A3, BoNT/A4, and BoNT/A5. The BoNT/B subtypes encompass, for instance, BoNT/B1, BoNT/B2, BoNT/B3, BoNT/B4, BoNT/B5, BoNT/B6, BoNT/B7 and BoNT/B8. The BoNT/C subtypes comprise, e.g., BoNT/C1-1 and BoNT/C1-2. Encompassed is also the BoNT/D-C subtype. The BoNT/E subtypes include, e.g., BoNT/E1, BoNT/E2, BoNT/E3, BoNT/E4, BoNT/E5, BoNT/E6, BoNT/E7, BoNT/E8 and BoNT/E9. Further, the BoNT/F subtypes comprise, for instance, BoNT/F1, BoNT/F2, BoNT/F3, BoNT/F4, BoNT/F5, BoNT/F6, and BoNT/F7. Further subtypes are described, e.g., in Hill et al. (J Bacteriol. 2007 February; 189(3): 818-32. Epub 2006 Nov. 17), the disclosure content of which is incorporated herewith by reference The neurotoxin polypeptide and, in particular, its light chain and heavy chain are derivable from one of the antigenically different serotypes of Botulinum neurotoxins or subtypes indicated above. In an aspect, said light and heavy chain of the neurotoxin polypeptide are the light and heavy chain of a neurotoxin selected from the group consisting of: BoNT/A, BoNT/B, BoNT/C1, BoNT/D, BoNT/E, BoNT/F, BoNT/G, BoNT/H or TeNT. In another aspect, the polynucleotide encoding said neurotoxin polypeptides comprises a nucleic acid sequence as shown in SEQ ID NO: 1 (BoNT/A), SEQ ID NO: 3 (BoNT/B), SEQ ID NO: 5 (BoNT/C1), SEQ ID NO: 7 (BoNT/D), SEQ ID NO: 9 (BoNT/E), SEQ ID NO: 11 (BoNT/F), SEQ ID NO: 13 (BoNT/G) or SEQ ID NO: 15 (TeNT). Moreover, encompassed is, in an aspect, a polynucleotide comprising a nucleic acid sequence encoding an amino acid sequence as shown in any one of SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) or SEQ ID NO: 16 (TeNT). Further encompassed is in an aspect of the methods of the present invention, a neurotoxin polypeptide comprising or consisting of an amino acid sequence selected from the group consisting of: SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) and SEQ ID NO: 16 (TeNT). Also encompassed is the corresponding nucleic and amino acid sequence of the recently described BoNT/H as shown, e.g., in Dover, N. et al., (2014), J Infect Dis 209(2): 192-202.

In another aspect, the said polynucleotide is a variant of the aforementioned polynucleotides or polypeptides. The variant can be a naturally occurring neurotoxin polynucleotide or polypeptide, such as the aforementioned Clostridial neurotoxin isoforms or subtypes. For example, it is recognized by those of skill in the art that within each serotype of Botulinum neurotoxin there can be naturally occurring Botulinum neurotoxin variants that differ somewhat in their amino acid sequence, and also in the nucleic acids encoding these proteins.

The variant can also be a non-naturally occurring neurotoxin polypeptide. As used herein, the term "non-naturally occurring variant" of a Clostridial neurotoxin means a Clostridial neurotoxin produced with the aid of human manipulation, including, without limitation, Clostridial neurotoxin produced by genetic engineering or recombinant methods, e.g., using random mutagenesis or rational design, enzymatically modified variants of Clostridial neurotoxins that are modified by the activity of enzymes, such as endo- or exoproteolytic enzymes, or Clostridial neurotoxins produced by chemical synthesis. "Genetic manipulation" refers to methods known in the art for modifying the native Clostridial neurotoxin of any serotype/subtype by means of modifying the gene encoding for the Clostridial neurotoxin or respective nucleic acids like DNA or mRNA. Recombinant methods for genetic engineering of a polynucleotide encoding a neurotoxin polypeptide or a neurotoxin polypeptide are well described in the art; see, e.g. Sambrook, J. & Russell, D. (2001). Molecular Cloning: a Laboratory Manual, 3rd edn. Cold Spring Harbor, N.Y.: Cold Spring Harbor Laboratory.

Moreover, a naturally or non-naturally occurring variant polynucleotide as referred to herein shall in another aspect comprise a nucleic acid sequence variant being at least 40%, at least 50%, at least 60%, at least 70%, at least 75%, at least 80%, at least 85%, at least 90%, at least 95%, at least 96%, at least 97%, at least 98% or at least 99% identical to the nucleic acid sequence as shown in any one of SEQ ID NOs: 1, 3, 5, 7, 9, 11, 13 or 15, or the nucleic acid sequence of BoNT/H as shown in in Dover, N. et al., (2014), J Infect Dis 209(2): 192-202, or a nucleic acid sequence variant which encodes an amino acid sequence being at least 40%, at least 50%, at least 60%, at least 70%, at least 75%, at least 80%, at least 85%, at least 90%, at least 95%, at least 96%, at least 97%, at least 98% or at least 99% identical to the amino acid sequence as shown in any one of SEQ ID NOs: 2, 4, 6, 8, 10, 12, 14, or 16, or the amino acid sequence of BoNT/H as shown in in Dover, N. et al., (2014), J Infect Dis 209(2): 192-202. The term "identical" as used herein refers to sequence identity characterized by determining the number of identical amino acids between two nucleic acid sequences or two amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence, e.g. the light chain or heavy chain of the neurotoxin polypeptide or both. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. In an aspect, each of the aforementioned variant polynucleotides encodes a polypeptide retaining one or more and, in another aspect, all of the herein defined biological properties of the respective neurotoxin polypeptide, i.e. the BoNT/A, BoNT/B, BoNT/C1, BoNT/D, BoNT/E, BoNT/F, BoNT/G, BoNT/H or Tetanus neurotoxin (TeNT). Those of skill in the art will appreciate that full biological activity is maintained only after proteolytic activation, even though it is conceivable that the unprocessed precursor can exert some biological functions or be partially active. In vivo assays for assessing the biological activity of a Clostridial neurotoxin include the mouse LD50 assay and the ex vivo mouse hemidiaphragm assay, as described by Pearce et al. (Pearce 1994, Toxicol. Appl. Pharmacol. 128: 69-77) and Dressler et al. (Dressler 2005, Mov. Disord. 20:1617-1619, Keller 2006, Neuroscience 139: 629-637). The biological activity is commonly expressed in Mouse Units (MU). As used herein, 1 MU is the amount of neurotoxic component, which kills 50% of a specified mouse population after intraperitoneal injection, i.e. the mouse i.p. LD50. In a further aspect, the variant polynucleotides can encode neurotoxins having improved or altered biological properties, e.g., they may comprise cleavage sites which are improved for enzyme recognition, and/or may be improved for receptor binding, internalization, translocation across the endosomal membrane into the cytosol or endoproteolytic cleavage of the corresponding substrate of the SNARE protein family.

Non-limiting examples of non-naturally occurring Clostridial neurotoxin variants include, e.g., conservative Clostridial neurotoxin variants. As used herein, the term "conservative Clostridial neurotoxin variant" means a Clostridial neurotoxin that has at least one amino acid substituted by another amino acid or an amino acid analog that has at least one property similar to that of the original amino acid from the reference Clostridial neurotoxin sequence as set forth elsewhere herein, e.g. the amino acid sequence shown in SEQ ID NO. 2, 4, 6, 8, 10, 12, 14 or 16 or the amino acid sequence of BoNT/H as shown in Dover, N. et al., (2014), J Infect Dis 209(2): 192-202. The variant may have one, two, three, four, five or even more conservative amino acid substitutions compared to the reference sequence. The variant shall have comparable or even improved properties of the reference Clostridial neurotoxin sequence. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. Preferably, the property is a biological property as defined elsewhere herein, i.e. (a) receptor binding, (b) internalization, (c) translocation across the endosomal membrane into the cytosol, and/or (d) endoproteolytic cleavage of proteins involved in synaptic vesicle membrane fusion. A conservative Clostridial neurotoxin variant can function in substantially the same manner as the reference Clostridial neurotoxin on which the conservative Clostridial neurotoxin variant is based, and can be substituted for the reference Clostridial neurotoxin in any aspect of the present invention. The Clostridial neurotoxin described herein will typically contain naturally occurring amino acid residues, but in some cases non-naturally occurring amino acid residues may also be present. Therefore, so-called "peptide mimetics" and "peptide analogues", which may include non-amino acid chemical structures that mimic the structure of a particular amino acid or peptide, may also be used within the context of the invention. Such mimetics or analogues are characterized generally as exhibiting similar physical characteristics such as size, charge or hydrophobicity, and the appropriate spatial orientation that is found in their natural peptide counterparts. A specific example of a peptide mimetic compound is a compound in which the amide bond between one or more of the amino acids is replaced by, for example, a carbon-carbon bond or other non-amide bond, as is well known in the art; see, for example Sawyer, in Peptide Based Drug Design, pp. 378-422, ACS, Washington D.C. 1995.

The neurotoxin polypeptide variant as used herein further encompasses chemically modified neurotoxin polypeptides. "Chemical modification" as used herein refers generally to methods known in the art for modifying the native or recombinant Clostridial neurotoxin of any serotype or subtype by means of chemical reactions or the like; it refers especially to substitutions, deletions, insertions, additions or posttranslational modifications of amino acids of the Clostridial neurotoxin. A chemically modified neurotoxin polypeptide may be one that is modified by pyruvation, phosphorylation, sulfatation, lipidation, pegylation, glycosylation and/or the chemical addition of an amino acid or a polypeptide comprising, e.g., between about two and about 500 amino acids. For example, by incorporating hyaluronic acid or polyvinylpyrrolidone or polyethyleneglycol or mixtures thereof into the neurotoxin polypeptide, the Clostridial neurotoxin, or the toxin which is derived from Clostridial toxin by chemical modification or by genetic manipulation, can be stabilized.

Another non-naturally occurring variant of the Clostridial neurotoxin which can be used in the methods of the invention is a hybrid Clostridial neurotoxin. In one aspect, the hybrid Clostridial neurotoxin comprises a combination of a Clostridial neurotoxin heavy chain and light chain, wherein the light chain and heavy chain are not of the same serotype or subtype.

Methods for making such chemically, enzymatically or genetically modified variants of Clostridial neurotoxins, and methods for identifying whether such variants maintain the biological properties referred to herein, such as (a) receptor binding, (b) internalization, (c) translocation across the endosomal membrane into the cytosol, and/or (d) endoproteolytic cleavage of proteins involved in synaptic vesicle membrane fusion, are well known to anyone of ordinary skill in the art; see, e.g., Sambrook, loc. cit.

The term "biological activity of a neurotoxin polypeptide" as used herein means the biological properties characteristic for a neurotoxin polypeptide, namely, a) receptor binding, (b) internalization, (c) translocation across the endosomal membrane into the cytosol, and/or (d) endoproteolytic cleavage of proteins involved in synaptic vesicle membrane fusion. It is envisaged that the neurotoxin polypeptide as used herein exhibits at least one of the properties a) to d) mentioned above, preferably endoproteolytic cleavage of proteins involved in synaptic vesicle membrane fusion, or two or three or all four biological properties listed in a) to d)). Assays for determining the biological activity of neurotoxin polypeptides are well known in the art and also described elsewhere herein; see, e.g., Pellett et al. (2011), Biochem. Biophys. Res. Commun. 404, 388-392; Whitemarsh et al. (2012), Toxicol. Sci. 126, 426-35.

SNAP-25 is a known substrate of and cleaved by BoNT/A, BoNT/C1 and BoNT/E. VAMP/Synaptobrevin is a substrate of and cleaved by BoNT/B, BoNT/D, BoNT/F, BoNT/G and TeNT, whereas Syntaxin is a substrate of and cleaved by BoNT/C1. The mentioned substrates and the corresponding nucleic acid and amino acid sequences are well known in the art; see, e.g., WO 2014/207109.

As used herein, the term "cell" refers to any eukaryotic cell susceptible to neurotoxin intoxication by a neurotoxin such as, e.g., BoNT/A, or any eukaryotic cell that can uptake a neurotoxin. Aspects of the present disclosure comprise, in part, a cell from an established cell line. The term "cell" encompasses cells from a variety of organisms, such as, e.g., murine, rat, porcine, bovine, equine, rhesus, primate and human cells; from a variety of cell types such as, e.g., neuronal and non-neuronal; and can be isolated from or part of a heterogeneous cell population, tissue or organism. It is to be understood that human embryonic cells are excluded from the scope of the methods of the invention. As used herein, the term "established cell line" is synonymous with "immortal cell line," or "transformed cell line" and refers to a cell culture of cells selected for indefinite propagation from a cell population derived from an organism, tissue, or organ source. By definition, an established cell line excludes a cell culture of primary cells. As used herein, the term "primary cells" are cells harvested directly from fresh tissues or organs and do not have the potential to propagate indefinitely. For example, primary neuronal cells can be used in the methods of the invention. An established cell line can comprise a heterogeneous population of cells or a uniform population of cells. An established cell line derived from a single cell is referred to as a clonal cell line. An established cell line can be one whose cells endogenously express all component necessary for the cells to undergo the overall cellular mechanism whereby a neurotoxin, such as BoNT/A, proteolytically cleaves a substrate, such as SNAP-25, and encompasses the binding of a neurotoxin to a neurotoxin receptor, such as BoNT/A, to a BoNT/A receptor, the internalization of the neurotoxin/receptor complex, the translocation of the neurotoxin light chain from an intracellular vesicle into the cytoplasm and the proteolytic cleavage of a neurotoxin substrate. Alternatively, an established cell line can be one whose cells have had introduced from an exogenous source at least one component necessary for the cells to undergo the overall cellular mechanism whereby a neurotoxin, such as BoNT/A, proteolytically cleaves a substrate, such as SNAP-25, and encompasses the binding of a neurotoxin to a receptor, such as BoNT/A to a BoNT/A receptor, the internalization of the neurotoxin/receptor complex, the translocation of the neurotoxin light chain from an intracellular vesicle into the cytoplasm and the proteolytic cleavage of a neurotoxin substrate. Also referred to as a genetically-engineered cell line, cells from such an established cell line may, e.g., express an exogenous FGFR2, an exogenous FGFR3, an exogenous SV2, an exogenous neurotoxin substrate such as SNAP-25, or any combination thereof.

"Cell culture" as used herein refers in the broadest sense to the removal of cells from an animal or human and their subsequent growth in a favourable artificial environment. The cells may be removed from the tissue directly and disaggregated by enzymatic or mechanical means before cultivation, or they may be derived from a cell line or cell strain that has already been established. Primary culture refers to the stage of the culture after the cells are isolated from the tissue and proliferated under the appropriate conditions until they occupy all of the available substrate, i.e. reach confluence. At this stage, the cells have to be subcultured, i.e. passaged by transferring them to a new vessel with fresh growth medium to provide more room for continued growth. Normal cells usually divide only a limited number of times before losing their ability to proliferate, which is a genetically determined event known as senescence; these cell lines are known as finite. However, some cell lines become immortal through a process called transformation, which can occur spontaneously or can be chemically or virally induced. When a finite cell line undergoes transformation and acquires the ability to divide indefinitely, it becomes a continuous cell line. Culture conditions vary widely for each cell type, but the artificial environment in which the cells are cultured invariably consists of a suitable vessel containing the following: a substrate or medium that supplies the essential nutrients (amino acids, carbohydrates, vitamins, minerals), growth factors, hormones, gases ($O_2$, $CO_2$), a regulated physico-chemical environment (pH, osmotic pressure, temperature) etc. Most cells are anchorage-dependent and must be cultured while attached to a solid or semi-solid substrate (adherent or monolayer culture), while others can be grown floating in the culture medium (suspension culture).

The term "cell(s) susceptible to neurotoxin intoxication" as denoted herein means a cell that can undergo the overall cellular mechanisms whereby a neurotoxin polypeptide (e.g., BoNT/A) cleaves a neurotoxin substrate (e.g., the BoNT/A substrate SNAP-25) and encompasses the binding of the neurotoxin polypeptide to its corresponding receptor (e.g., binding of BoNT/A to the BoNT/A receptor), the internalization of the neurotoxin/receptor complex, the translocation of the neurotoxin light chain from an intracellular vesicle into the cytoplasm and the proteolytic cleavage of the neurotoxin substrate. Accordingly, a "cell susceptible to neurotoxin intoxication" as used herein means a neurotoxin sensitive cell. The mentioned term comprises a cell or a cell line, for example, an isolated, primary cell or a cell line thereof or a cell of an established cell line or an established cell line, for example, tumor cells or tumor cell lines which are capable of differentiating to neuronal cells, such as neuroblastoma cells or neuroblastoma cell lines as defined elsewhere herein. For example, said neuroblastoma cell line can be a SiMa cell line which is commercially available from DSMZ (ACC 164). Specific clones of the cell line SiMa are furthermore disclosed in WO 2010/105234. Other neuroblastoma cell lines which can be used in the method of the invention can be obtained from ATCC or DSMZ, under the following ATCC or DSMZ numbers: Cell line N1E-115 under CRL-2263, cell line Neuro2a under CCL-131, cell line SH-SYSY under CRL-2266, cell line PC12 under CRL-1721, cell line MHH-NB-11 under ACC 157 (DSMZ) and cell line SK-N-BE(2) under CRL-2271. Other tumor cells which are susceptible to neurotoxin intoxication are P-19 cells (murine embryonal carcinoma cell line) (DSMZ no. ACC 316). In some aspects, e.g. for activity assays, it can be necessary to differentiate said cells into neuronal cells. Such differentiation methods are well described in the literature. Further encompassed by cells susceptible to neurotoxin intoxication are induced pluripotent stem cell (iPS)-derived neurons, preferably human induced pluripotent stem cell (iPS)-derived neurons; see, e.g., Whitemarsh et al. (2012), loc. cit. Such human iPS-derived neurons are also commercially available, for instance, from Cellular Dynamics. Methods of generating iPS cells are described, for example, in Yu et al. (Science 2009 May 8; 324(5928): 797-801. Epub 2009), WO 2011/056971 and WO 2011/025852. In some aspects, iPS are differentiated into neurons using suitable methods, e.g., those described in WO 2012/135621 and U.S. Patent Applications US 2010/0279403 and US 2010/0216181.

The terms "differentiation", "differentiating" or "differentiated" as used herein denote the process by which an unspecialized or a relatively less specialized cell becomes relatively more specialized. In the context of cell ontogeny, the adjective "differentiated" is a relative term. Hence, a "differentiated cell" is a cell that has progressed further down a certain developmental pathway than the cell it is being compared with. A differentiated cell may, for example, be a terminally differentiated cell, i.e., a fully specialized cell that takes up specialized functions in various tissues and organs of an organism, and which may but need not be post-mitotic. For instance, iCell® neurons are terminally differentiated from human iPS cells and exhibit neuronal characteristics and functions. In another example, a differentiated cell may also be a progenitor cell within a differentiation lineage, which can further proliferate and/or differentiate. Similarly, a cell is "relatively more specialized" if it has progressed further down a certain developmental pathway than the cell it is being compared with, wherein the latter is therefore considered "unspecialized" or "relatively less specialized". A relatively more specialized cell may differ from the unspecialized or relatively less specialized cell in one or more demonstrable phenotypic characteristics, such as, for example, the presence, absence or level of expression of particular cellular components or products, e.g., RNA, proteins, specific cellular markers or other substances, activity of certain biochemical pathways, morphological appearance, proliferation capacity and/or kinetics, differentiation potential and/or response to differentiation signals, etc., wherein such characteristics signify the progression of the relatively more specialized cell further along the said developmental pathway. Cell culture conditions for differentiating cells into neuronal cells are well known in the art as evident from the literature cited herein.

Furthermore, cell culture conditions for incubating cells susceptible to neurotoxin intoxication with a neurotoxin polypeptide for a time and under conditions which allow for the neurotoxin polypeptide to exert its biological activity are well described in the art and can also be derived from the publications recited herein.

The term "specific uptake of a neurotoxin polypeptide" as used herein means a process in which the neurotoxin polypeptide enters the neuron by binding to its specific neuronal membrane receptor(s), for example, SV2, ganglio sides, GD1a, Synaptotagmin II for BoNT/B, or Synaptotagmin I for BoNT/D/-C, being taken up into an endosome-like compartment and penetrating the endosome membrane via a pH-dependent translocation process. Accordingly, the mentioned term encompasses a) receptor binding of the neurotoxin polypeptide, (b) internalization of the neurotoxin polypeptide, and (c) translocation of the neurotoxin polypeptide across the endosomal membrane into the cytosol. As appreciated by those skilled in the art, the neurotoxin-sensitive cell is preferably able to first uptake a neurotoxin and then undergoes the overall cellular mechanisms listed above. The expression "non-specific or unspecific uptake of a neurotoxin polypeptide" as denoted herein means a process in which the neurotoxin polypeptide or a degradation product thereof enters the neuron by binding to non-specific neuronal membrane receptor(s) or by entering the cell via unspecific mechanisms, e.g. by an accidental co-transport in the event of pinocytosis. A neurotoxin-sensitive cell as used herein can uptake, e.g., about 100 nanomolar (nM), about 10 nM, about 1 nM, about 500 picomolar (pM), about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 9 pM, about 8 pM, about 7 pM, about 6 pM, about 5 pM, about 4 pM, about 3 pM, about 2 pM, about 1 pM, about 0.5 pM, or about 0.1 pM of neurotoxin polypeptide or less than one of the indicated values. EC50 values above 100 pM have been reported in the literature. By definition, a cell susceptible to neurotoxin intoxication must express, or be engineered to express, at least one neurotoxin receptor and at least one neurotoxin substrate. Receptors and substrates for neurotoxins are described in the art and mentioned elsewhere herein. Accordingly, said cell is preferably susceptible to a biologically active or mature neurotoxin polypeptide as defined herein. Preferably, the neurotoxin-sensitive cell as used herein is susceptible to neurotoxin intoxication by, e.g., about 1 nM or less, 500 pM or less, about 400 pM or less, about 300 pM or less, about 200 pM or less, about 100 pM or less, about 90 pM or less, about 80 pM or less, about 70 pM or less, about 60 pM or less, about 50 pM or less, about 40 pM or less, about 30 pM or less, about 20 pM or less, about 10 pM or less, about 9 pM or less, about 8 pM or less, about 7 pM or less, about 6 pM or less, about 5 pM or less, about 4 pM or less, about 3 pM or less, about 2 pM or less, about 1 pM or less, about 0.9 pM or less, about 0.8 pM or less, about 0.7 pM or less, about 0.6 pM or less, about 0.5 pM or less, about 0.4 pM or less, about 0.3 pM or less, about 0.2 pM or less, or even about 0.1 pM or less. As known in the art, the "half maximal effective concentration (EC50)" refers to the concentration of a drug, antibody or toxicant which induces a response halfway between the baseline and maximum after some specified exposure time. It is commonly used as a measure of a drug's potency. The EC50 of a graded dose response curve therefore represents the concentration of a compound where 50% of its maximal effect is observed. The EC50 of a quantal dose response curve represents the concentration of a compound where 50% of the population exhibits a response, after a exposure duration. Methods for the identification of cells or cell lines susceptible to neurotoxin intoxication and/or having neurotoxin uptake capacity, i.e. neurotoxin-sensitive cells as defined herein, are known in the art; see, e.g. US 2012/0122128 A1. The biological activity of the neurotoxin polypeptides, in an aspect, results from all of the aforementioned biological properties. Only a few cell-based assays with sufficient high sensitivity towards neurotoxins which can be used for the determination of the biological activity of a neurotoxin have been described in the prior art so far, as indicated elsewhere herein.

The term "enhancing" as utilized herein means that the specific uptake of a neurotoxin polypeptide into the cell is improved or increased, in comparison to Clostridial neurotoxin intoxication not using (i) $K^+$-mediated depolarization of the cells, (ii) a reduced neurotoxin polypeptide exposition time and (iii) agitation of the cells during neurotoxin polypeptide exposition. The specific uptake of a neurotoxin polypeptide into the cell is preferably increased at least 1.5-fold, at least 2-fold, at least 3-fold, at least 4-fold, at least 5-fold, at least 6-fold, at least 7-fold, at least 8-fold, at least 9-fold or even at least 10-fold, in comparison to methods using cell culture conditions that do not comprise (i) $K^+$-mediated depolarization of the cells, (ii) a reduced neurotoxin polypeptide exposition time and (iii) agitation of the cells during neurotoxin polypeptide exposition. Generally, the methods described in the art use a final concentration of $K^+$ of about 5 mM, a neurotoxin polypeptide exposition time of about 72 hours and no agitation of the cells. It has found by the present inventors that the above measures (i), (ii) and/or (iii) not only improve the specific uptake of the neurotoxin into the cells but also result in a reduced unspecific uptake of the mentioned neurotoxin or degradation products into the cells. The nonspecific uptake of a neurotoxin polypeptide into the cell is preferably reduced at least 1.5-fold, at least 2-fold, at least 3-fold, at least 4-fold, at least 5-fold, at least 6-fold, at least 7-fold, at least 8-fold, at least 9-fold or even at least 10-fold, in comparison to methods using cell culture conditions that do not comprise (i) $K^+$-mediated depolarization of the cells, (ii) a reduced neurotoxin polypeptide exposition time and/or (iii) agitation of the cells during neurotoxin polypeptide exposition. Means and methods for measuring the specific or unspecific uptake of a neurotoxin polypeptide into the cell are well described in the literature and herein and further shown in the following examples. For example, the effect of BoNT/A, BoNT/C and BoNT/E neurotoxin exposure on SNAP-25 proteolysis in neuronal cell cultures can be used as an indicator of neurotoxin translocation. The same holds true for BoNT/C neurotoxin exposure on Syntaxin proteolysis in neuronal cells and BoNT/E, BoNT/D and BoNT/G neurotoxin exposure on VAMP proteolysis.

The aforementioned method of the invention is followed by a method for determining the biological activity of the neurotoxin polypeptide in the cells, in a further aspect of the method of the invention.

As demonstrated in the following examples, a cell-based potency assay could advantageously be improved by increasing the specific uptake of Clostridial neurotoxin polypeptides into the cells, by using $K^+$-mediated depolarization of the cells, a reduced neurotoxin polypeptide exposition time and/or agitation of the cells during neurotoxin polypeptide exposition. At the same time, a decreased unspecific uptake of the mentioned neurotoxin or degradation products into the cells could be observed.

A number of assays for determining the biological activity of neurotoxin polypeptides has been described in the art, such as light chain assays (ELISA), Endopep-MS, FRET, HPLC-UPLC, DARET or cell-based assays using, for instance, SH-SY5Y or Neuro2a cells, embryonic chicken neurons, primary neurons from spinal cord or dorsal root ganglia (Pellett et al. (2011), Biochem. Biophys. Res. Commun. 404, 388-392), embryonic stem cell-derived neurons (Whitemarsh et al. (2012), Toxicol. Sci. 126, 426-35) relying on Western blot read-out, or differentiated human neuroblastoma SiMa cells; see, e.g. Fernández-Salas, E. et al., (2012). PLoS One 7 (11).

In a second aspect, the invention provides for a method for directly determining the biological activity of a neurotoxin polypeptide in cells, comprising:
  a) incubating cells susceptible to neurotoxin intoxication with a neurotoxin polypeptide for a time and under conditions which allow for the neurotoxin polypeptide to exert its biological activity, the incubation comprising at least one of the following steps: (i) $K^+$-mediated depolarization of the cells, (ii) a reduced neurotoxin polypeptide exposition time and/or (iii) agitation of the cells during neurotoxin polypeptide exposition;

b) fixing the cells and, optionally, permeabilizing the cells with a detergent;

c) contacting the cells with at least a first capture antibody specifically binding to the non-cleaved and neurotoxin-cleaved substrate and with at least a second capture antibody specifically binding to the cleavage site of the neurotoxin-cleaved substrate, under conditions which allow for binding of said capture antibodies to said substrates;

d) contacting the cells with at least a first detection antibody specifically binding to the first capture antibody, under conditions which allow for binding of said first detection antibody to said first capture antibody, thus forming first detection complexes and with at least a second detection antibody specifically binding to the second capture antibody, under conditions which allow for binding of said second detection antibody to said second capture antibody, thus forming second detection complexes;

e) determining the amount of the first and second detection complexes of step d); and f) calculating the amount of substrate cleaved by said neurotoxin polypeptide in said cells by means of the second detection complexes, thereby determining the biological activity of said neurotoxin polypeptide in said cells.

Preferably, this method is an in vitro method. This method of the invention allows for the direct determination of the biological activity of a neurotoxin polypeptide in cells. This means that no lysis of the cells and no isolation or concentration of the cleaved neurotoxin substrate from cell lysates is necessary any longer, as in the methods described in the art. For example, in the Western blot analysis-based assay of the art, the neurotoxin substrate is concentrated by the separation and concentration of the components of the respective sample in the SDS polyacrylamide gel. In the ECL sandwich ELISA described in the art, the concentration of the neurotoxin substrate is carried out by using antibodies which bind specifically to the cleaved neurotoxin substrate on a microtiter plate to which the cell lysate is added. The cleaved neurotoxin substrate is isolated from the lysate by binding of the mentioned antibody which results in a concentration of said cleaved Clostridial neurotoxin substrate.

In contrast, the cleaved neurotoxin substrate, for example SNAP-25, can be directly detected in the cell, in this method of the invention. To this end, cells which are susceptible to neurotoxin intoxication as defined in more detail elsewhere herein are incubated with a neurotoxin polypeptide for a time and under conditions which allow for the neurotoxin polypeptide to exert its biological activity. The incubation comprises K$^+$-mediated depolarization of the cells, a reduced neurotoxin polypeptide exposition time and/or agitation of the cells during neurotoxin polypeptide exposition, as set forth elsewhere herein. These measures enhance the specific cellular uptake of the neurotoxin while at the same time reducing the unspecific uptake of the neurotoxin or degradation products into the cells. In a next step, the cells are fixed, for example, by addition of a fixation agent such as methanol, ethanol, acetone, formaldehyde or mixtures of the mentioned fixation agents. Optionally, the cells can be permeabilized by using at least one detergent such as Triton X-100, Tween 20, Saponin, Digitonin or n-Octyl-β-glucopyranoside. The detergent can be comprised in an appropriate buffer such as PBS. Thereafter, the cells are contacted with at least a first capture antibody which specifically binds to the non-cleaved and neurotoxin-cleaved substrate and with at least a second capture antibody specifically binding to the cleavage site of the neurotoxin-cleaved substrate, under conditions which allow for binding of said capture antibodies to said substrates. Herein, the first capture antibody is able to determine the total content or amount of neurotoxin substrate in the cells, by binding specifically to an appropriate epitope present in both the non-cleaved and neurotoxin-cleaved neurotoxin substrate. The second capture antibody recognizes and binds specifically to an epitope present only in the cleaved neurotoxin substrate, for example, by binding specifically to the neurotoxin-cleaved site in the neurotoxin substrate. Alternatively, the cells can be contacted with a mixture of said first and second capture antibodies, i.e. the cells are contacted with at least a first capture antibody and at least a second capture antibody simultaneously, under the mentioned conditions. In the next step, the cells are contacted with at least a first detection antibody specifically binding to the first capture antibody under conditions which allow for binding of said first detection antibody to said first capture antibody, thus forming first detection complexes. In a subsequent step, the cells are contacted with at least a second detection antibody specifically binding to the second capture antibody, under conditions which allow for binding of said second detection antibody to said second capture antibody, thus forming second detection complexes. Alternatively, the cells can be contacted with a mixture of said first and second detection antibodies, i.e. the cells are contacted with at least a first detection antibody and at least a second detection antibody simultaneously, under the mentioned conditions. Alternatively, after permeabilization of the cells, they can be contacted with a mixture of said first and second capture antibodies and said first and second detection antibodies simultaneously, under the mentioned conditions. In the next step, the amounts of the first and second detection complexes are determined. Finally, the amount of substrate cleaved by said neurotoxin polypeptide in said cells is calculated by means of the second detection complexes. Thereby, the biological activity of said neurotoxin polypeptide is determined directly in the cells.

In the following, this method of the invention is described in more detail. For cell culture, the cells susceptible to neurotoxin intoxication as defined herein, such as neuronal cells, SiMa cells or iPS-derived neurons, are first seeded on 96-well microtiter plates. SiMa cells are differentiated to a neuronal phenotype, for example, according to the procedures disclosed in WO 2010/105234, and iPS-derived neurons are differentiated to a neuronal phenotype, e.g., according to assays described in WO 2012/135621. Then, the cells are incubated with a neurotoxin polypeptide, such as BoNT/A for a time and under conditions which allow for the neurotoxin polypeptide to exert its biological activity. The incubation comprises K$^+$-mediated depolarization of the cells, a reduced neurotoxin polypeptide exposition time and/or agitation of the cells during neurotoxin polypeptide exposition, as described elsewhere herein.

In the subsequent step, the cells are fixed on the microtiter plate, prior to the ELISA assay. For fixing the cells, for example ice-cold methanol (−20° C.) can be added to the cells for 20 minutes at −20° C.

For performing the ELISA assay, the cells are first washed. As a wash buffer, e.g., 0.1% Triton X-100 in 10 mM PBS buffer (pH 7.4) can be used. Thereafter, endogenous proteases are quenched by a quenching buffer such as 0.6% H$_2$O$_2$ in 10 mM PBS (pH 7.4), followed by another wash step. In the following step, free binding sites on the microtiter plate are blocked by an appropriate blocking buffer such as, for instance, 2% BSA in 10 mM PBS buffer (pH 7.4) and 0.05% Triton X-100. Then, the cells are permeabilized, by using an appropriate detergent. As a permeabilization buffer, e.g., 0.5% Triton X-100 in 10 mM PBS buffer can be utilized. Permeabilization allows the diffusion of the antibodies through the pores formed in the cells. Thereafter, the cells are washed by washing buffer as mentioned above.

In the next step, the permeabilized cells are incubated, e.g., with a mixture of two different antibodies. The mixture comprises a first capture antibody specifically binding to the non-cleaved and neurotoxin-cleaved substrate and a second capture antibody specifically binding to the cleavage site of the neurotoxin-cleaved substrate. Said first and second capture antibodies can also be applied subsequently. For example, the first capture antibody can specifically bind to both non-cleaved and neurotoxin-cleaved SNAP-25, thereby allowing for the quantification of the total amount or content of SNAP-25 in the cells. Further, this first capture antibody can be used for the normalization of the amount of cleaved SNAP-25 in the cells, upon evaluation. The second capture antibody specifically binds to the cleavage site of the neurotoxin-cleaved substrate and therefore allows the determination and detection of the cleaved neurotoxin substrate, such as BoNT/A-cleaved SNAP-25.

The following detection of the total neurotoxin substrate and the neurotoxin-cleaved neurotoxin substrate in the method of the invention can be carried out directly on the microtiter plate or cell culture dish, i.e. within the cells. Advantageously, it is, therefore, not necessary to prepare cell extracts and to isolate and/or concentrate the neurotoxin substrate from the cell lysate in the method of the invention, as in the methods described in the art. Thereafter, the cells are washed in order to remove excess antibody not bound to the respective antigen. In the subsequent step, the permeabilized cells are contacted with at least a first detection antibody and at least a second detection antibody. Said antibodies can be applied as a mixture, i.e. simultaneously, or subsequently. The first detection antibody specifically binds to the first capture antibody. Thereby, first detection complexes are being formed. The first detection antibody can be directed against the species from which the first capture antibody is derived from. For example, in case the rabbit polyclonal anti-SNAP-25 antibody S9684 (Sigma) is used as a first capture antibody specifically binding to the non-cleaved and BoNT/A-cleaved substrate SNAP-25, an anti-rabbit alkaline phosphatase-conjugated antibody can be used as a first detection antibody. The second detection antibody specifically binds to the second capture antibody. Thereby, second detection complexes are being formed. The second detection antibody can be directed against the species from which the second capture antibody is derived from. For instance, in case the mouse monoclonal antibody (mAb) 20-2-5 described WO 2014/207109 in is used as a second capture antibody specifically binding to the BoNT/A-cleaved SNAP-25, an anti-mouse horseradish peroxidase (HRP)-conjugated antibody can be used as a second detection antibody. It is evident to those skilled in the art that the first detection antibody and the second detection antibody are conjugated with different enzymes in order to allow for the specific detection of the respective first and second capture antibody as used in the method of the invention. For instance, the HRP-based detection as described elsewhere herein can be used for the BoNT/A-cleaved SNAP-25 and the alkaline phosphatase-based detection for the total (BoNT/A-cleaved and non-cleaved) SNAP-25. Thereafter, the cells are washed again. In a subsequent step, a fluorogenic HRP substrate is added to the cells. As a HRP substrate, e.g., Amplex UltraRed (Invitrogen) can be used which is excited at 540 nm and which emits at 600 nm. Incubation with the HRP substrate is carried out for a time sufficient for sufficient conversion of substrate by the horseradish peroxidase. Subsequent to the incubation with the HRP substrate, for example, the AP substrate DiFMUP (6,8-difluoro-4-methylumbelliferyl phosphate; excitation 360 nm; emission 450 nm) can be added to the HRP substrate and the cells are incubated with a mixture of said two substrates. Incubation with said AP substrate is carried out for a time which allows for sufficient conversion of substrate by the alkaline phosphatase. As known in the art, a substrate has to be converted in an amount which is sufficient so that the measured signal is at least as high as the mean value of the blank plus three standard deviations of the mean, according to the definition of limit of detection. The limit of detection can be determined as described in the literature; see, e.g., Armbruster and Pry, Clinical Biochem. Rev. 2008, 29 (Supplement 1): S49-S52. Because the pH optimum of the alkaline phosphatase is in the alkaline region, the corresponding substrate buffer is strongly alkaline. If the alkaline phosphatase substrate is added to the HRP substrate, the reaction of the horseradish peroxidase is stopped by the alkaline pH and the alkaline phosphatase converts DiFMUP. Converted HRP substrate is not influenced by the alkaline pH. Finally, the fluorescence of the two substrates is measured as follows:

Amplex UltraRed: Excitation 540 nm; emission 600 nm
DiFMUP: Excitation 360 nm; emission 450 nm As appreciated by those skilled in the art, only those fluorogenic substrates are appropriate for detection of the first and second capture antibody in the method of the invention which exhibit different excitation/emission wave lengths of the used substrates. Only in this case, they allow for the specific detection of each antigen, i.e. the total neurotoxin substrate (such as non-cleaved and neurotoxin-cleaved SNAP-25) and the cleaved neurotoxin substrate (such as neurotoxin-cleaved SNAP-25). Thereby, it is possible to quantify the total content of neurotoxin substrate and the content of cleaved neurotoxin substrate in every well or cell culture dish at the same time. In light of this, it is advantageously possible to automatize the method of the invention. As set forth elsewhere herein it is envisaged that the fluorogenic substrates chosen for the method of the invention exhibit a sufficient shift between the excitation/emission spectra in order to allow for the specific detection of the respective substrate. This requirement is fulfilled, for example, for the HRP substrate Amplex and its derivatives and for the AP substrate DiFMUP. Whereas, in an optimal case, there is no overlap between the excitation/emission spectra of the used fluorogenic substrates, it has been experienced that an overlap of up to 30% in the peak area of the excitation spectra of the used fluorogenic substrates is tolerable. Further details as regards this method of the invention are described, e.g., in WO 2014/207109.

As further acknowledged by those skilled in the art, the method of the present invention allows for the direct detection and quantification of neurotoxin substrate cleaved by the neurotoxin polypeptide in the cells, thereby determining the biological activity of said neurotoxin polypeptide in said cells. Advantageously, the method of the invention does not require the preparation of cell lysates or extracts and the isolation or concentration of the cleaved neurotoxin substrate from the cell lysates/extracts, which is necessary for the methods known in the art. As a consequence of this, sample material can be saved. Further, the sample preparation and the number of samples can be reduced by the method of the invention since the amount of total neurotoxin substrate and the amount of cleaved neurotoxin substrate in the sample can be determined at the same time. In the assays described in the art, the samples have to be subdivided in order to detect both antigens, i.e. total neurotoxin substrate and cleaved neurotoxin substrate, separately from each other. The method of the invention renders the subdivision of the sample unnecessary. Thereby, inhomogeneities resulting from the subdivision of samples can be avoided and sample material can be saved. Furthermore, antigens can be degraded in the assays described in the art which can falsify the detection of the cleaved neurotoxin substrate. This is because in the assays described in the art, the cells are incubated with detergent-containing lysis buffers which, however, are not able to inactivate the neurotoxin polypeptide or other endogenous proteases resulting in degradation of the neurotoxin substrate upon longer storage of the samples. Stronger lysis buffers cannot be used in the ECL sandwich ELISA described in the prior art due to the required use of the cell lysate in said assay. This is because the aggregation of the above-mentioned antigens can result in unspecific adsorption of the antigens to the plastic surface of the cell culture dishes or microtiter plates which in turn disturbs the detection of the antigens by appropriate antibodies. Since the antibodies for the detection of the antigens get into contact with the lysate, too, the antibodies can also aggregate. In this case, no reliable and accurate detection of the antigen is possible anymore. The present inventors have experienced such degradation reactions by using Western blot assays for the detection of the biological activity of neurotoxin activity described in the art. Upon longer storage of lysates at −20° C., in comparison to fresh lysate samples the detection signal of total SNAP-25 has been found to be strongly reduced and the ratio of cleaved neurotoxin substrate SNAP-25 to un-cleaved neurotoxin substrate SNAP-25 had shifted due to degradation processes during the freezing. It has been found by the present inventors that the degradation of the neurotoxin substrate and/or the instability of the samples can be avoided by directly fixing the cells on the cell culture dish because both the neurotoxin substrate and the neurotoxin or other endogenous proteases are inactivated immediately by aggregation on the cell culture dish. This can be achieved by using, for example, fixing of the cells by methanol or other fixatives or fixation agents known in the art, such as ethanol, acetone, formaldehyde or mixtures thereof or other fixation agents described herein. The analysis of the stability of, e.g., parental SiMa cells (human neuroblastoma cells; DSMZ no.: ACC 164) and iPS-derived neurons (Whitemarsh et al. (2012), Toxicol. Sci. 126, 426-35) using this fixation method did not reveal any differences between fresh and cell culture dishes stored seven days in the refrigerator.

Suitable antibodies specifically binding to the non-cleaved and neurotoxin-cleaved substrate which can be used as first capture antibody in the method of the invention encompass, e.g., the rabbit polyclonal anti-SNAP-25 antibody S9684 (Sigma), the rabbit polyclonal anit-SNAP25 antibody PAS-19708 (Pierce Antibodies), the rabbit polyclonal anti-SNAP25 antibody PAS-19701 (Pierce Antibodies), or the rabbit monoclonal anti-SNAP25 antibody ab108990 (Abcam).

Appropriate antibodies specifically binding to the cleavage site of the neurotoxin-cleaved substrate that can be utilized as second capture antibody in the method of the invention include, for example, the mouse monoclonal antibody clone 20-2-5 (WO 2014/207109), the mouse monoclonal antibody described in EP 14199282.6, the mouse monoclonal antibody MC-6053 (clone 4F3-2C1, R&D Systems), MAB4733 (Abnova), orb26633 (Biorbyt), or GWB-T00279 (Genway).

Suitable detection antibodies that can be used as first and second detection antibodies are known in the art. For example, the first detection antibody can be an alkaline phosphatase (AP)-conjugated antibody, a horseradish-peroxidase (HRP)-conjugated antibody or an antibody conjugated to a fluorescence dye. As a second detection antibody, e.g., an alkaline phosphatase (AP)-conjugated antibody, a horseradish-peroxidase (HRP)-conjugated antibody, a glucose oxidase-conjugated antibody, a tyrosinase-conjugated antibody or a β-Galactosidase antibody can be used. Preferably, the first and second detection antibodies differ from each other, when used in the method of the invention.

As used herein, the singular forms "a", "an" and "the" include both singular and plural reference unless the context clearly dictates otherwise. By way of example, "a cell" refers to one or more than one cell.

As used herein, the term "about" when qualifying a value of a stated item, number, percentage, or term refers to a range of plus or minus 10 percent, 9 percent, 8 percent, 7 percent, 6 percent, 5 percent, 4 percent, 3 percent, 2 percent, 1 percent or 0 percent of the value of the stated item, number, percentage, or term. Preferred is a range of plus or minus 10 percent.

The terms "comprising", "comprises" and "comprised of" as used herein are synonyms with "including", "includes" or "containing", "contains", and are inclusive or open-ended and do not exclude additional, non-recited members, elements or method steps. Evidently, the term "comprising" encompasses the term "consisting of". More specifically, the term "comprise" as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase "consisting of" means that the composition (or device, or method) has the recited elements (or steps) and no more. In contrast, the term "comprises" can encompass also a method including further steps, e.g., steps d) and e), in addition to steps a), b) and c).

In case numerical ranges are used herein such as "in a concentration between 1 and 5 micromolar", the range includes not only 1 and 5 micromolar, but also any numerical value in between 1 and 5 micromolar, for example, 2, 3 and 4 micromolar.

The term "in vitro" as used herein denotes outside, or external to, the animal or human body. The term "in vitro" as used herein should be understood to include "ex vivo". The term "ex vivo" typically refers to tissues or cells removed from an animal or human body and maintained or propagated outside the body, e.g., in a culture vessel. It is preferred, that the methods of the invention are in vitro methods. The term "in vivo" as used herein denotes inside, or internal to, the animal or human body.

In a further aspect of the methods of the invention, the $K^+$-mediated depolarization of the cells is carried out at an additional $K^+$ concentration of about 20 mM to about 55 mM, for at least 2 hours.

Usually, the cell culture medium used in the art contains 5 mM K. Accordingly, the final concentration of $K^+$ in the methods of the invention is preferably between about 25 mM and about 60 mM $K^+$.

In a still further aspect of the methods of the invention, the K⁺-mediated depolarization of the cells and/or the neurotoxin polypeptide exposition is carried out in the presence of GT1b.

In another aspect of the methods of the invention, GT1b is used in a concentration between 15 and 50 µM, preferably 20 µM.

In a further aspect of the methods of the invention, the reduced neurotoxin polypeptide exposition time is exposition of the cells to the neurotoxin polypeptide for at least 24 hours and less than 96 hours, preferably for at least 48 hours and 72 hours at maximum.

In a further aspect of the methods of the invention, agitation of the cells during neurotoxin polypeptide exposition is achieved with a magnetic stirrer or rotating spinner flasks or shaking of the cells. Agitation of the cells is carried out at an appropriate cell culture medium flow rate, preferably a mean (or average) medium flow rate of about 25 cm/min to about 300 cm/min, more preferably of about 25 cm/min to about 150 cm/min.

In a further aspect of the methods of the invention, the K⁺-mediated depolarization of the cells is carried out at an additional K⁺ concentration of at least about 20 mM to about 55 mM, for at least 2 hours in the presence of 20 µM GT1b and neurotoxin polypeptide, followed by neurotoxin polypeptide exposition for additional 70 hours under agitation.

In a further aspect of the methods of the invention, an incubation time without neurotoxin polypeptide precedes the neurotoxin polypeptide exposition.

In a further aspect of the methods of the invention, the incubation time without neurotoxin polypeptide is between 16 and 48 hours.

In a further aspect of the methods of the invention, the method is a fluorescence method.

In a further aspect of the methods of the invention, the neurotoxin polypeptide is BoNT/A, BoNT/B, BoNT/C1, BoNT/D, BoNT/E, BoNT/F, BoNT/G, BoNT/F, BoNT/G, BoNT/H or TeNT, or subtypes thereof as defined elsewhere herein.

In a further aspect of the methods of the invention, the substrate is VAMP/Synaptobrevin, SNAP-25 or Syntaxin.

In a further aspect of the methods of the invention, the cells are neuronal cells or neuronal differentiated cells selected from the group consisting of: primary neuronal cells, tumor cells which are capable of differentiating to neuronal cells such as neuroblastoma cells, P19 cells or induced pluripotent stem cell (IPS)-derived neurons.

Further preferred embodiments of the methods of the invention can be derived from the following examples.

The FIGURE shows:

FIG. 1: Kinetics in loss of activity of stressed drug product samples. Drug product samples containing BoNT/A were stored at 70° C. for up to four weeks. After 0, 1, 2 and 4 weeks samples were drawn and subjected to analysis in the mouse $LD_{50}$ bioassay as well as in the cell based assay (CBA) employing different protocols. On the x-axis the storage time in weeks is given whereas on the y-axis the relative potency is given. The potency at the start point was set to 100% and the consecutive test time points are expressed relative to the start point. The values for the $LD_{50}$ bioassay are depicted as diamonds. The cell based assays protocol employing K⁺-depolarization is depicted in squares, the protocol employing an 8 hour toxin incubation time followed by a 64 hour toxin-free incubation time is depicted in triangles and the protocol employing shaking during the 72 hour incubation time is depicted in circles. A CBA protocol which was not modified is depicted in line symbols. In sum, FIG. 1 shows a comparison of three cell based assay examples where the stressed samples show a comparable kinetic in decay to the referenced assay, the mouse $LD_{50}$ bioassay.

The invention will now be illustrated by the following examples which shall, however, not be construed as limiting the scope of the present invention.

EXAMPLES

Example 1: Double-Fluorescence-Cell Based-BoNT/A Activity ELISA

Fixation of Cells
1. Remove the media/toxin solution. Add 100 µl/well ice-cold methanol (−20° C.) and incubate for 20 min at −20° C.

Note: Perform all subsequent steps at room temperature.
After Cell Fixation:
1. Remove the methanol solution and add 100 µl/well PBS buffer. For longer storage (>1 day) one should add 300 µl//well PBS buffer and seal the plates with parafilm. The plates should be stored in the refrigerator.
2. Remove the PBS buffer and wash the cells 3 times with 200 µl/well of PBS buffer. Each step should be performed for 1 minute with gentle shaking.
3. Remove the PBS buffer and add 100 µl/well of quenching buffer and incubate for 20 minutes with gentle shaking.
4. Remove the quenching buffer and wash the cells once with 300 µl/well of PBS buffer for 3 minutes under gentle shaking.
5. Remove the PBS buffer, and add 200 µl/well of blocking buffer and incubate for 1 hour with gentle shaking.
6. Remove the blocking buffer and add 100 µl of the primary antibody mixture (antibody dilution in blocking buffer) to each well. Incubate overnight (16-18 h) with gentle shaking. The cells are simultaneously incubated with two primary antibodies: a mouse antibody specific for the BoNT/A-cleaved SNAP-25 and a polyclonal rabbit antibody that recognizes SNAP-25 (antibody for determining the total amount of SNAP 25 for normalization).
7. Remove the primary antibody mixture and wash the cells 4 times with 200 µl of PBS buffer. Each step should be performed for 3 minutes with gentle shaking.
8. Remove the PBS buffer, and add 100 µl of the secondary antibody mixture: HRP-conjugated anti-mouse and AP-conjugated anti-rabbit secondary antibodies (antibody dilution in blocking buffer) to each well and incubate for 2.5 to 3 hours with gentle shaking.
9. Remove the secondary antibody mixture and wash the cells 5 times with 200 µl/well of PBS buffer, followed by 1 washing step with 300 µl/well of HEPES buffer. Each wash step should be performed for 3 minutes with gentle shaking.
10. Remove the HEPES buffer from the plate and add 75 µl of a fluorogenic substrate for horseradish-peroxidase (HRP substrate) to each well. Incubate for 50 minutes with gentle shaking. Protect the plates from direct light.
11. Add 75 µl of a fluorogenic substrate for alkaline phosphatase (AP substrate) to each well and incubate for an additional 50 minutes at with gentle shaking. Protect the plates from direct light.
12. Read the plates using a fluorescence plate reader:
excitation at 540 nm; emission at 600 nm.
excitation at 360 nm; emission at 450 nm.
13. Calculation
For normalization, the RFU value for cleaved SNAP-25 (fluorescence at 600 nm) is normalized to RFU of total SNAP-25 (450 nm) in each well. For better illustration of RFUs in a diagram all values are multiplied with a factor 1000 using the following equation:

$$\frac{RFU\,(600\text{ nm})}{RFU\,(450\text{ nm})} \times 1000$$

Subsequently the resulting RFU values are averaged for each standard or sample.
Reagent Preparation
PBS buffer (10 mM):
Phosphate buffered saline (Sigma, # P5368) (pH 7.4)
Quenching Buffer:
0.6% $H_2O_2$ in 10 mM PBS buffer (pH 7.4)
Blocking Buffer:
2% BSA in 10 mM PBS buffer (pH 7.4)+0.05% Triton X-100
HEPES buffer:
50 mM HEPES (pH 7.4)
HRP Substrate:
50 mM HEPES (pH 7.4)
0.007% H2O2
150 pM Amplex UltraRed
AP Substrate:
25 mM Diethanolamine (pH 9.8)
2 mM $MgCl_2$
100 µl M DiFMUP Example 2: Enhancement of Specific Uptake of Clostridial Neurotoxin Polypeptides into Cells a) iCell® neurons were thawed and plated according to the Cellular Dynamics International (CDI) user manual on 96 well plates from 4 different cell batches. 24 hours (h) after plating the medium was replaced by fresh maintenance medium as described in the user manual.

After further 72 h incubation time, the medium was removed and replaced by fresh medium containing BoNT/A in varying concentrations and $K^+$-ions in a total concentration of 30 mM, (i.e. 25 mM additional $K^+$ compared to the medium as such). After 2 hours the high-$K^+$-medium was removed and fresh medium containing BoNT/A in varying concentrations was added to the cells.

Another 70 h later, the medium was aspirated, the cells were fixed and an ELISA readout was performed as described in Example 1. The results of this protocol are given in FIG. 1, squares.

b) iCell® neurons were thawed and plated according to the Cellular Dynamics International (CDI) user manual on 96 well plates from 4 different cell batches. 24 hours (h) after plating the medium was replaced by fresh maintenance medium as described in the user manual.

After further 72 h incubation time, the medium was removed and replaced by fresh medium containing BoNT/A in varying concentrations. After 8 hours the BoNT/A-containing-medium was removed and fresh medium without BoNT/A was added to the cells.

Another 64 h later, the medium was aspirated, the cells were fixed and an ELISA readout was performed as described in Example 1. The results of this protocol are given in FIG. 1, triangles.

c) iCell® neurons were thawed and plated according to the Cellular Dynamics International (CDI) user manual on 96 well plates from 4 different cell batches. 24 hours (h) after plating the medium was replaced by fresh maintenance medium as described in the user manual.

After further 72 h incubation time, the medium was removed and replaced by fresh medium containing BoNT/A in varying concentrations. The cells were put on a plate shaker in the incubator and were shaken at an average flow rate of 300 cm/min during toxin exposition time.

Another 72 h later, the medium was aspirated, the cells were fixed and an ELISA readout was performed as described in Example 1. The results of this protocol are given in FIG. 1, circles.

d) iCell® neurons were thawed and plated according to the Cellular Dynamics International (CDI) user manual on 96 well plates from 4 different cell batches. 24 hours (h) after plating the medium was replaced by fresh maintenance medium as described in the user manual.

After further 72 h incubation time, the medium was removed and replaced by fresh medium containing BoNT/A in varying concentrations.

Another 72 h later, the medium was aspirated, the cells were fixed and an ELISA readout was performed as described in Example 1. The results of this protocol are given in FIG. 1.

CONCLUSION

In sum, $K^+$-mediated depolarization of the cells, a reduced neurotoxin polypeptide exposition time or agitation of the cells during neurotoxin polypeptide exposition facilitate comparable stability indicating kinetics of the cell based assay of Example 1 when compared to the mouse $LD_{50}$ bioassay.

The invention claimed is:

1. A method for enhancing the specific uptake of a neurotoxin polypeptide into cells, the method comprising: incubating cells susceptible to neurotoxin intoxication with a neurotoxin polypeptide for a time and under conditions which allow for the neurotoxin polypeptide to exert its biological activity, the incubation comprising at least two of the following steps: (i) $K^+$-mediated depolarization of the cells, (ii) a reduced neurotoxin polypeptide exposition time and/or (iii) agitation of the cells during neurotoxin polypeptide exposition, thereby enhancing the specific uptake of the neurotoxin polypeptide into said cells.

2. The method of claim 1, followed by determining the biological activity of the neurotoxin polypeptide in the cells.

3. A method for directly determining the biological activity of a neurotoxin polypeptide in cells, comprising:

a) incubating cells susceptible to neurotoxin intoxication with a neurotoxin polypeptide for a time and under conditions which allow for the neurotoxin polypeptide to exert its biological activity, the incubation comprising at least two of the following steps: (i) K$^+$-mediated depolarization of the cells, (ii) a reduced neurotoxin polypeptide exposition time and/or (iii) agitation of the cells during neurotoxin polypeptide exposition;

b) fixing the cells and, optionally, permeabilizing the cells with a detergent;

c) contacting the cells with at least a first capture antibody specifically binding to a non-cleaved and neurotoxin-cleaved substrate and with at least a second capture antibody specifically binding to the cleavage site of the neurotoxin-cleaved substrate, under conditions which allow for binding of said capture antibodies to said substrates;

d) contacting the cells with at least a first detection antibody specifically binding to the first capture antibody, under conditions which allow for binding of said first detection antibody to said first capture antibody, thus forming first detection complexes and with at least a second detection antibody specifically binding to the second capture antibody, under conditions which allow for binding of said second detection antibody to said second capture antibody, thus forming second detection complexes;

e) determining the amount of the first and second detection complexes of step d); and f) calculating the amount of substrate cleaved by said neurotoxin polypeptide in said cells by means of the second detection complexes, thereby determining the biological activity of said neurotoxin polypeptide in said cells.

4. The method of claim 3, wherein the K$^+$-mediated depolarization of the cells is carried out at an additional K$^+$ concentration of about 20 mM to about 55 mM, for at least 2 hours.

5. The method of claim 3, wherein the K$^+$-mediated depolarization of the cells and/or the neurotoxin polypeptide exposition is carried out in the presence of GT1b.

6. The method of claim 5, wherein GT1b is used in a concentration between 15 and 50 µM.

7. The method of claim 3, wherein the reduced neurotoxin polypeptide exposition time is exposition of the cells to the neurotoxin polypeptide for at least 24 hours and less than 96 hours.

8. The method of claim 3, wherein agitation of the cells during neurotoxin polypeptide exposition is carried out with a magnetic stirrer, rotating spinner flasks or shaking of the cells by a shaker.

9. The method of claim 3, wherein the K$^+$-mediated depolarization of the cells is carried out at an additional K$^+$ concentration of about 20 mM to about 55 mM, for at least 2 hours in the presence of 20 µM GT1b and neurotoxin polypeptide, followed by neurotoxin polypeptide exposition for additional 70 hours under agitation.

10. The method of claim 3, wherein an incubation time without neurotoxin polypeptide precedes the neurotoxin polypeptide exposition.

11. The method of claim 10, wherein the incubation time without neurotoxin polypeptide is between 16 and 48 hours.

12. The method of claim 3, wherein the method is a fluorescence method.

13. The method of claim 3, wherein the neurotoxin polypeptide is BoNT/A, BoNT/B, BoNT/C1, BoNT/D, BoNT/E, BoNT/F, BoNT/G, BoNT/H, or subtypes thereof.

14. The method of claim 3, wherein the substrate is VAMP/Synaptobrevin, SNAP-25 or Syntaxin.

15. The method of claim 3, wherein the cells are neuronal cells or neuronal differentiated cells selected from the group consisting of: primary neuronal cells, tumor cells which are capable of differentiating to neuronal cells, P19 cells or induced pluripotent stem cell (IPS)-derived neurons.

16. The method of claim 1, wherein the K$^+$-mediated depolarization of the cells is carried out at an additional K$^+$ concentration of about 20 mM to about 55 mM, for at least 2 hours.

17. The method of claim 1, wherein the K$^+$-mediated depolarization of the cells and/or the neurotoxin polypeptide exposition is carried out in the presence of GT1b.

18. The method of claim 1, wherein the reduced neurotoxin polypeptide exposition time is exposition of the cells to the neurotoxin polypeptide for at least 24 hours and less than 96 hours.

19. The method of claim 1, wherein agitation of the cells during neurotoxin polypeptide exposition is carried out with a magnetic stirrer, rotating spinner flasks or shaking of the cells by a shaker.

20. The method of claim 1, wherein the K$^+$-mediated depolarization of the cells is carried out at an additional K$^+$ concentration of at least about 20 mM to about 55 mM, for at least-2 hours in the presence of 20 µM GT1b and neurotoxin polypeptide, followed by neurotoxin polypeptide exposition for additional 70 hours under agitation.

21. The method of claim 1, wherein an incubation time without neurotoxin polypeptide precedes the neurotoxin polypeptide exposition.

22. The method of claim 1, wherein the neurotoxin polypeptide is BoNT/A, BoNT/B, BoNT/C1, BoNT/D, BoNT/E, BoNT/F, BoNT/G, BoNT/H, or subtypes thereof.

23. The method of claim 1, wherein the cells are neuronal cells or neuronal differentiated cells selected from the group consisting of: primary neuronal cells, tumor cells which are capable of differentiating to neuronal cells, P19 cells or induced pluripotent stem cell (IPS)-derived neurons.

24. The method of claim 15, wherein the tumor cells which are capable of differentiating to neuronal cells are neuroblastoma cells.

25. The method of claim 23, wherein the tumor cells which are capable of differentiating to neuronal cells are neuroblastoma cells.

* * * * *